United States Patent
Bidle et al.

(10) Patent No.: US 9,217,741 B2
(45) Date of Patent: *Dec. 22, 2015

(54) BIOACTIVE COMPOUNDS FROM PHYTOPLANKTON CONTAINING GLYCOSIDIC RESIDUE FOR APOPTOSIS AND CANCER TREATMENT

(75) Inventors: Kay Daniel Bidle, Lawrenceville, NJ (US); Assaf Vardi, Haifa (IL); Benjamin A. S. Van Mooy, Falmouth, MA (US); Helen F. Fredricks, Rochester, MA (US); Liti Haramaty, East Brunswick, NJ (US)

(73) Assignees: Woods Hole Oceangraphic Institution, Woods Hole, MA (US); Rutgers, The State University of New Jersey, New Brunswick, NJ (US)

( * ) Notice: Subject to any disclaimer, the term of this patent is extended or adjusted under 35 U.S.C. 154(b) by 952 days.

This patent is subject to a terminal disclaimer.

(21) Appl. No.: 12/940,927

(22) Filed: Nov. 5, 2010

(65) Prior Publication Data

US 2011/0129851 A1 Jun. 2, 2011

Related U.S. Application Data

(60) Provisional application No. 61/258,423, filed on Nov. 5, 2009.

(51) Int. Cl.
*G01N 33/50* (2006.01)

(52) U.S. Cl.
CPC ........ *G01N 33/5097* (2013.01); *G01N 33/5044* (2013.01); *G01N 2510/00* (2013.01)

(58) Field of Classification Search
CPC ........... C12Q 1/6806; C12Q 2527/125; C12Q 2527/137; C12Q 1/025; C12Q 1/68; C12Q 1/6813; A61K 2300/00; A61K 35/74; A61K 36/00; A61K 38/00; G01N 2510/00; G01N 33/92; G01N 33/5044; G01N 33/5097; A01N 1/021

See application file for complete search history.

(56) References Cited

U.S. PATENT DOCUMENTS

| | | | |
|---|---|---|---|
| 5,821,072 A | 10/1998 | Schwartz et al. | |
| 6,656,729 B2 | 12/2003 | Bathurst et al. | |
| 6,793,945 B2 | 9/2004 | Bathurst et al. | |
| 2010/0145084 A1 | 6/2010 | Bidle et al. | |

FOREIGN PATENT DOCUMENTS

WO WO-2010/005560 1/2010

OTHER PUBLICATIONS

Wilson et al., "Complete Genome Sequence and Lytic Phase Transcription Profile of a Coccolithovirus", Science 309:1090-1092 (2005).

Allen et al., Proteomic analysis of the EhV-86 virion. Proteome Sci 6:11 (2008).
Allen et al., Use of microarrays to assess viral diversity: from genotype to phenotype. Environmental Microbiology 9(4): 971-982 (2007).
Allen, Locus-Specific Gene Expression Pattern Suggests a Unique Propagation Strategy for a Giant Algal Virus. J. Virology 80(15) 7699-7705 (2006).
Bidle and Bender, Iron Starvation and Culture Age Activate Metacaspases and Programmed Cell Death in the Marine Diatom Thalassiosira pseudonana. Eukaryotic Cell 7:223-236 (2008).
Bidle et al. Cell death in planktonic, photosynthetic microorganisms. Nature Rev. Microbiol. 2:643-655 (2004).
Bidle et al., Viral activation and recruitment of metacaspases in the unicellular coccolithophore, Emiliania huxleyi. PNAS 104(14):6049-6054 (2007).
Brussaard et al, Virus-like particles in a summer bloom of Emiliana huxleyi in the North Sea. Aquat Microb Ecol 10: 105-113 (1996).
Brussaard, Viral Control of Phytoplankton Populations—a Review. J. Eukaryotic Microbiol. 51(2): 125-138 (2004).
Brügger et al., The HIV lipidome: A raft with an unusual composition. Proc. Natl. Acad. Sci. USA. 103(8): 2641-2646 (2006).
Evans, C. et al "Changes in Emiliania huxleyi fatty acid profiles during infection with E-huxleyi virus 86: physiological and ecological implications" Aquatic Microbial Ecology 55(3): 219-228 (2009).
Fuhrman, Marine viruses and their biogeochemical and ecological effects. Nature vol. 399, 541-548 (1999).
Grassme et al., Host defense against Pseudomonas aeruginosa requires ceramide-rich membrane rafts. Nat Med 9(3): 322-330 (2003).
Han, G. et al "Expression of a novel marine viral single-chain serine palmitoyltransferase and construction of yeast and mammalian single-chain chimera" The Journal of Biological Chemistry 281(52): 39935-39942 (2006).
Khuruna et al., Apoptosis in plant disease response : A close encounter of the pathogen kind. Current Science, 88 (5) 740-752 (2005).
Koga et al., Cerebrosides A and C, Sphingolipid Elicitors of Hypersensitive Cell Death and Phytoalexin Accumulation in Rice Plants. J. Biol. Chem. 273, 31985 (1998).
Koopman et al., Annexin V for flow cytometric detection of phosphatidylserine expression on B cells undergoing apoptosis. Blood 84,5, 1415-1420 (1994).
Lowe et al. p53-dependent apoptosis modulates the cytotoxicity of anticancer agents. (1993) Cell 74:95 7-697.
Lynch et al. An introduction to plant sphingolipids and a review of recent advances in understanding their metabolism and function *New Phytol.* 161, 677 (2004).

(Continued)

*Primary Examiner* — Debbie K Ware
(74) *Attorney, Agent, or Firm* — Melissa Hunter-Ensor; Saul Ewing LLP

(57) ABSTRACT

Phytoplankton represent a potential source of bioactive compounds. The present disclosure provides, inter alia, methods for identifying glycerolipids and apoptosis-inducing sphingosine-like lipids from virally-infected phytoplankton.

10 Claims, 14 Drawing Sheets

(56) References Cited

OTHER PUBLICATIONS

Molinski et al., Drug development from marine natural products. Nature Reviews/Drug Discovery vol. 8, 69-85 (2009).

Parker et al., Genomic Insights into Marine Microalgae Annu. Rev. vol. 42, 619-645 (2008).

Reiter et al., Viral killer toxins induce caspase-mediated apoptosis in yeast. JCB 168(3) 353-358 (2005).

Richier et al., Light-Dependent Transcriptional Regulation of Genes of Biogeochemical Interest in the Dipliod and Haploid Life Cycle Stages of Emiliania huxleyi. Applied and Environmental Microbiology 75(10): 3366-3369 (2009).

Sakamoto et al., Host sphingolipid biosynthesis as a target for hepatitis C virus therapy. Nat Chem Biol 1(6): 333-337 (2005).

Schroeder et al., Coccolithovirus (Phycodnaviridae): Characterization of a new large dsDNA algal virus that infects Emiliana huxleyi. (abstract) Archives of Virology 147(9) [retrieved Mar. 5, 2012] Retrieved from Internet < URL: http://www.springerlink.com/content/29uj6cb2qbhv3ugb/abstract/?target=print.

Sturt et al., Intact polar membrane lipids in prokaryotes and sediments deciphered by high-performance liquid chromatography/electrospray ionization multistage mass spectrometry—new biomarkers for biogeochemistry and microbial ecology. Rapid Communications in Mass Spectrometry vol., 18, 617-628 (2004).

Suttle, Marine viruses—major players in the global ecosystem. Nature Reviews Microbiology, vol. 5, 801-812 (2007).

Suttle, Viruses in the sea. Nature vol., 15 356-361(2005).

Van Mooy et al., Phytoplankton in the ocean use non-phosphorus lipids in response to phosphorus scarcity. Nature vol. 458 69-72 (2009).

Van Mooy et al., Sulfolipids dramatically decrease phosphorus demand by picocyanobacteria in oligotrophic marine environments. Proc. Natl Acad. Sci. USA 103, 8607 (2006).

Vardi et al., A Diatom Gene Regulating Nitric-Oxide Signaling and Susceptibility to Diatom-Derived Aldehydes. Curr. Biol. 18, 895 (2008).

Vardi et al., A Stress Surveillance System Based on Calcium and Nitric Oxide in Marine Diatoms. Plos Biology 4(3) 411-419 (2006).

Vardi et al., Programmed cell death of the dinoflagellate Peridinium gatunense is mediated by $CO_2$ limitation and oxidative stress. Curr. Biol. 9, 1061 (1999).

Vardi et al., Viral glycosphingolipids induce lytic infection and cell death in marine phytoplankton. Science, 326(5954): 861-5 (2009).

Vardi, A. et al. "Viral Sphingolipids Biomimic Infection via Induction of Coccolithophores Programmed Cell Death". (Abstract) In: 3rd Annual meeting of the SCOR Working Group on the Role of Viruses in Marine Ecosystems. May 14-16, 2009. University of Delaware. Newark, The United States of America. p. 38[retrieved Dec. 7, 2010]. Retrieved from Internet < URL: http://scor-viral-ecology.dbi.udel.edu/SCOR2009_meetingsprogram.pdf.

Vardi, A. et al. "Virally-Induced Sphingolipids Regulate Host Cell Fate in the Marine Coccolithophore, Emiliania Huxleyi" (Abstract) In: ASLO Aquatic Sciences Meeting 2009. Jan. 25-30, 2009. Centre de Congres Acropolis. Nice, France. [retrieved Dec. 7, 2010]. Retrieved from Internet < URL:http://www.sgmeet.com/aslo/nice2009/viewabstract2.asp?AbstractID=4839>.

Vaulot et al., The diversity of small eukaryotic phytoplankton (≤ 3 μm) in marine ecosystems. FEMS Microbiol Rev vol. 32, 795-820 (2008).

BIOACTIVE COMPOUNDS FROM PHYTOPLANKTON CONTAINING GLYCOSIDIC RESIDUE FOR APOPTOSIS AND CANCER TREATMENT

CROSS-REFERENCE TO RELATED APPLICATION

This application claims the benefit of U.S. Provisional Patent Application No. 61/258,423, filed Nov. 5, 2009, which is hereby incorporated by reference herein in its entirety.

STATEMENT ABOUT FEDERAL FUNDING

Work described herein was funded, in whole or in part, by Grant Nos. IOS-0717494, OCE-0646944, and OCE-0619608 awarded by the National Science Foundation (NSF) and Grant No. N00014-06-1-0134 awarded by the Office of Naval Research. The United States Government has certain rights in this invention.

BACKGROUND

Identification of drugs that modulate apoptosis is a major goal of the pharmaceutical and biotechnology industries. Apoptosis, or programmed cell death, serves many purposes in cell populations. Termination of damaged, stressed or infected cells conserves resources for healthy cells and may help to prevent spread of infection. In multicellular organisms, a changing environment often leads to cycles of cell proliferation or death, depending on the needs of the organism. Similarly, during development of multicellular organisms, excess cells are produced but later removed by apoptosis. Finally, the importance of apoptosis in the health of an organism is underscored by the consequences of excess apoptosis or lack of apoptosis. In humans, excess apoptosis is linked to autoimmune and neurodegenerative diseases, while a lack of apoptosis contributes to the uncontrolled growth of cancerous cells.

Because apoptosis is induced by signals external or internal to the cell, it is contemplated that identification and purification of select signals could provide useful compositions for modulating apoptosis in cell populations, multicellular organisms, and in human disease. Accordingly, there remains a need for identifying compositions that induce or inhibit apoptosis.

Marine organisms provide a vast source of natural products for use in pharmaceutical and biomedical applications. Many novel compounds have been identified in marine invertebrates, including potent anti-tumor and anti-mitotic compounds currently in clinical trials. Marine microorganisms, which represent an estimated 90% of the biomass in the ocean (Suttle, Nature Reviews Microbiology, Vol. 5, 801-812 (2007)), are also potential sources of novel chemical structures.

SUMMARY OF INVENTION

The present disclosure describes methods for isolating bioactive compounds from phytoplankton. The methods are based on the interaction observed between phytoplankton and lytic viruses, wherein viral infection of the phytoplankton induces production of lipids. Lipids may be sphingosine-like lipids and/or glycerolipids.

One aspect of the present disclosure provides a method for isolating one or more apoptosis-inducing lipids, such as sphingosine-like lipids, comprising: (a) obtaining a sample of one or more lipids from a virally-infected phytoplankton; (b) contacting a target cell with the sample; (c) assaying the target cell for apoptosis-associated activity in the presence of the sample; wherein apoptosis-associated activity in the target cell indicates that the sample comprises one or more apoptosis-inducing lipids.

The phytoplankton may be coccolithophores, such as $E.\ huxleyi$, and the virus may be a coccolithovirus, such as EhV86. The method may further comprise isolating the one or more apoptosis-inhibiting lipids from the sample, e.g., by chromatography, for example by HPLC, and may also comprise analyzing the one or more apoptosis-inducing lipids by mass spectrometry.

The target cells used in the present methods may be prokaryotic cells or eukaryotic cells. In various embodiments, the target cells may be phytoplankton cells, such as coccolithophores, e.g., $E.\ huxleyi$. A eukaryotic cell may be a plant cell or an animal cell, such as mammalian cell, e.g., a human cell.

The methods of the present disclosure also feature assays for apoptosis-associated activity. Apoptosis-associated activity may be apoptosis, a decrease in photosynthetic efficiency, an increase in expression of a caspase gene and/or an increase in caspase activity. Apoptosis-associated activity may also be cell shrinkage, DNA fragmentation, or membrane blebbing.

Sphingosine-like lipids, such as glycosylated sphingosine-like lipids, may induce apoptosis in cells. In some embodiments, glycosylated sphingosine-like lipids may be viral glycosylated sphingosine-like lipids.

The present disclosure also contemplates methods of manufacturing lipids using phytoplankton. In some embodiments, a method of manufacturing one or more sphingosine-like lipids may comprise infecting phytoplankton with a virus, culturing the infected phytoplankton, and isolating one or more sphingosine-like lipids, such as apoptosis-inducing sphingosine-like lipids, from the infected phytoplankton. In other embodiments, a method of manufacturing one or more glycerolipids may comprise infecting phytoplankton with a virus, culturing the infected phytoplankton, and isolating the one or more glycerolipids from the infected phytoplankton. The one or more glycerolipids may be capable of inhibiting apoptosis, such as viral-mediated apoptosis.

Another aspect of the present disclosure provides a method for isolating one or more lipids, such as glycerolipids, capable of inhibiting viral-mediated apoptosis, e.g., by obtaining a sample of one or more lipids from a virally-infected phytoplankton; contacting a target cell with the sample; and assaying the target cell for apoptosis-associated activity in the presence of the sample and in the presence of a stimulus that induces apoptosis in the target cell in the absence of the sample, wherein a decrease in apoptosis-associated activity in the target cell relative to the activity in the absence of the sample indicates that the sample comprises one or more lipids capable of inhibiting apoptosis. In some embodiments, the stimulus is a virus that infects the cell and induces apoptosis. In various embodiments, cell may be contacted with the sample before the virus infects the cell, or after the virus infects the cell.

The phytoplankton may be coccolithophores, e.g., $E.\ huxleyi$, and the virus may be a coccolithovirus, e.g., EhV86. The method may further comprise isolating one or more lipids from the sample, e.g., by chromatography, for example by HPLC, and may also comprise analyzing the one or more lipids by mass spectrometry.

The target cells used in the present methods may be prokaryotic cells or eukaryotic cells. Thus, the target cells may be phytoplankton cells, such as coccolithophores, e.g.,

*E. huxleyi*. A eukaryotic cell may be a plant cell or an animal cell, such as mammalian cell, and/or a human cell.

The methods of the present disclosure also feature assays for apoptosis-associated activity. Apoptosis-associated activity may be apoptosis, a decrease in photosynthetic efficiency, an increase in expression of a caspase gene and/or an increase in caspase activity. Apoptosis-associated activity may also be cell shrinkage, DNA fragmentation, or membrane blebbing.

In one embodiment of the present invention, a compound may have a structure of formula (I)

$$\text{Gly-O} \underset{\underset{R^5}{\overset{}{\diagdown}}\underset{O}{\overset{}{N}}\underset{OR^4}{\overset{}{\diagup}}\text{Alk}}{\overset{\overset{OR^1}{\overset{OR^2}{|}}\overset{OR^3}{|}}{\diagup\diagdown\diagup\diagdown\diagup\text{Aln}}} \quad (I)$$

or a pharmaceutically acceptable salt thereof, wherein
Gly is a glycosidic residue;
$R^1$, $R^2$, $R^3$, $R^4$ and $R^5$ are each independently selected from hydrogen, $C_{1-6}$alkyl, and $C_{1-6}$alkylcarbonyl, preferably hydrogen;
Aln is a $C_{2-25}$alkenyl group; and
Alk is a $C_{1-25}$alkyl group.

In another embodiment, a glycerolipid with apoptosis-inducing activity may have be characterized as having a mass spectra pattern substantially the same as that shown in FIGS. 8 and 9.

BRIEF DESCRIPTION OF DRAWINGS

FIG. 6 summarizes survival data of Ehux374 after treatment with lipid 802. In measures of photosynthetic health and cell growth, the cells treated with a 1:1000 dilution of lipid 802 show prolonged survival after viral infection, relative to untreated controls.

FIG. 9 shows the mass spectra from atmospheric pressure chemical ionization (APCI, direct infusion) of purified and derivatized glycocerebrosides.

FIG. 10 shows ion current chromatograms.

DETAILED DESCRIPTION

A. Overview

Figure 1A:
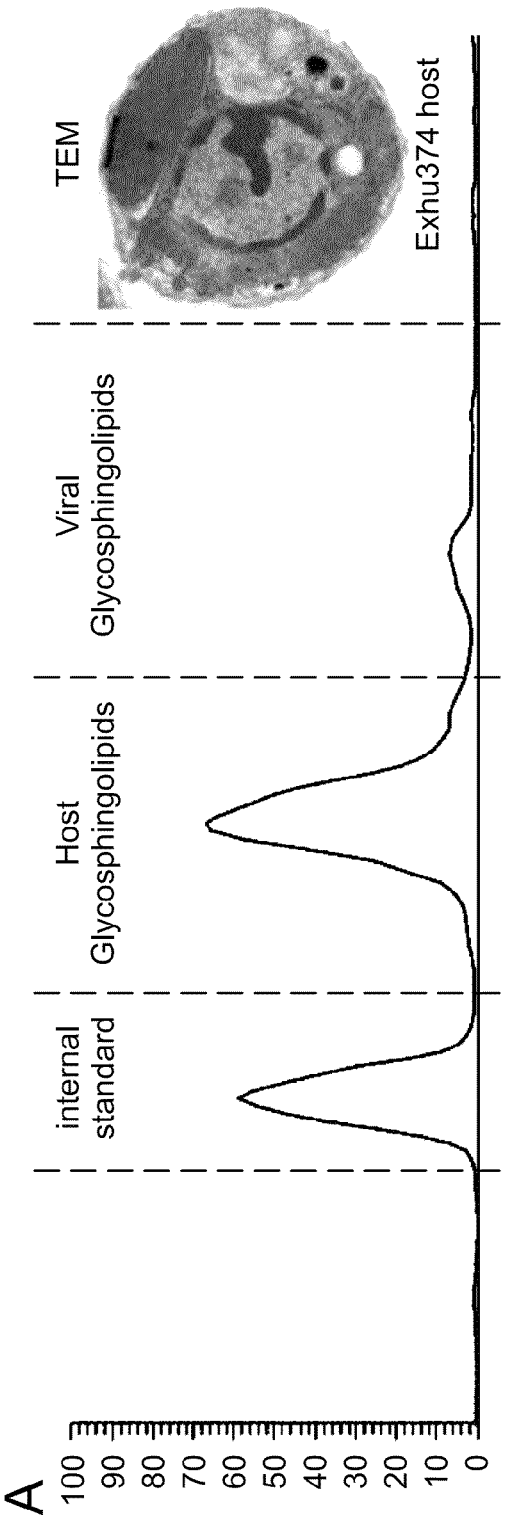
FIG. 1 shows the production of viral glycosylated sphingosine-like lipids (GSLs) in EhV86-infected *E. huxleyi* cells and in purified EhV86 virions. GSL summed ion HPLC/MS chromatograms showing relative abundances of GSLs extracted from susceptible Ehux374 (FIG. 1A), Ehux374 infected with EhV86 52 h post-infection (FIG. 1B), purified EhV86 on a $CsCl_2$ gradient (FIG. 1C), and resistant Ehux373 infected with EhV86 52 h post-infection (FIG. 1D). Peaks were normalized to internal standard. Pictured in the insets are transmission electron microscopy (TEM) images of respective treatments.

The present disclosure describes methods for the identification and production of sphingosine-like lipids, such as sphingosine-like lipids and glycerolipids from a virus-phytoplankton system. Sphingosine-like lipids are amino alcohols acylated by a fatty acid and comprise a fatty acid chain and a sphingosine-like portion. The sphingosine-like lipids induce apoptosis and/or apoptosis-associated activity in cells, while the glycerolipids inhibit viral-mediated apoptosis. Methods disclosed herein make use of the coevolutionary relationship between marine viruses and phytoplankton. Marine viruses that infect and terminate phytoplankton are recognized as a major ecological and evolutionary driving force, shaping community structure and nutrient cycling in the marine environment. The molecular interactions between phytoplankton and viruses are complex, and involve a suite of pathways comprising apoptosis, cell-signaling, cell metabolism, immune response, and lipid biosynthesis.

The molecules generated by this interaction may have potent bioactivities. The molecules produced are in addition to or in excess of what is contained in either the host phytoplankton or in the viruses that may infect them. The virus induces production of bioactive compounds in the infected phytoplankton, either by recruiting host machinery to generate viral molecules, or by triggering production of host molecules. Thus, the chemical composition of the combined phytoplankton/virus system may change during the course of viral infection.

Infected cells and/or surrounding culture media may be collected during the course of viral infection, and chemical extracts may be prepared. The extracts may contain chemically pure molecules, or mixtures of molecules. In some embodiments of the present disclosure, the lipid composition within the phytoplankton-virus system changes during the course of infection. In particular, a group of sphingosine-like lipids appears within 3.5 hours after infection, and levels of these sphingosine-like lipids rise in concert with apoptosis of the phytoplankton. As described herein, experiments in uninfected cells demonstrate that a preparation of isolated sphingosine-like lipids induces apoptosis in uninfected cells, indicating that the virus-phytoplankton system serves as a platform for producing and/or identifying apoptosis-inducing lipids, such as sphingosine-like lipids.

In other embodiments of the present disclosure, a group of glycerolipids (herein also called the 802 lipids) is generated, e.g., within 45 hours after infection. These glycerolipids tend to appear as a second group of glycerolipids (herein called the 830 lipids) disappears. As described herein, experiments demonstrate that a preparation of the 802 lipids inhibits viral-mediated apoptosis in a population of virus-infected cells. Thus, the virus-phytoplankton system also serves as a platform for producing and/or identifying lipids that inhibit viral-mediated apoptosis of cells.

A sample of lipids may be prepared by removing infected phytoplankton cells, pelleting the cells by centrifugation, and lysing the cells to access the membranes and/or intracellular contents. Fractions of phytoplankton may be enriched for endoplasmic reticulum, reticular body, mitochondria, Golgi apparatus, coccolith-producing compartments, plastids, chloroplasts, nuclei, membranes associated with these organelles, and/or the plasma membrane. Alternately, the sample of lipids may be prepared directly from the lysed cells, without further fractionation.

To identify other lipids that modulate apoptosis, samples of lipids (e.g., containing either sphingosine-like lipids or glycerolipids) extracted from virally-infected phytoplankton may be screened for their ability to induce apoptosis or inhibit apoptosis, such as viral-mediated apoptosis. When desired sphingosine-like lipids or glycerolipids have been identified, the present disclosure contemplates the use of the virus-phytoplankton system for manufacturing the desired lipids. Production of virally-infected phytoplankton may be scaled up, either in an open-pond system or in a bioreactor. Notably, cultured phytoplankton are widely used in the manufacture of food and cosmetics additives and are being further developed for large-scale production of biofuels.

1. Phytoplankton

Phytoplankton include a diverse assemblage of photosynthetic organisms, comprising both prokaryotic cyanobacteria and eukaryotic algae. Among the eukaryotic phytoplankton, the coccolithophores are one of the most abundant classes of unicellular phytoplankton, and often dominate the modern ocean. Coccolithophores belong to the phylum haptophytes, and possess calcium carbonate plates (or scales) called coccoliths. They are normally found in the surface euphotic zone of the ocean, and can be cultured in the laboratory setting.

*Emiliana huxleyi* is the most abundant and cosmopolitan species within the coccolithophores. *E. huxleyi* grow into massive annual blooms and die by metacaspase-mediated mechanisms (Bidle et al., PNAS 104(14): 6049-6054 (2007)). Generally, caspase-mediated death of phytoplankton may be a mechanism of programmed cell death in response to bacterial or viral infection, environmental stress or DNA damage from reactive oxygen species or UV exposure (Bidle and Falkowski. Nature Rev. Microbiol. 2:643-655 (2004), Parker et al., Ann. Rev. Genet. 42:619-45 (2008)).

In one aspect of the present disclosure, the phytoplankton used in the virus-phytoplankton system belong to the haptophyte phylum. Haptophytes typically have two slightly unequal flagella, and a unique organelle called a haptonema, which resembles a flagellum but differs in the arrangement of microtubules and in its use. The mitochondria have tubular cristae. Other well-known examples of haptophytes include *Pavlova lutheri* and *Isochysis galbana* which are used as a feed source for aquaculture, and coccolithophores, which are the most abundant of the haptophytes. The phytoplankton of the present methods may be coccolithophores, and further, may be *E. huxleyi*. The *E. huxleyi* may be any suitable virus-sensitive strain such as one of *E. huxleyi* strains 374, 92F, 1516, CCMP 1516, EH2, S. Africa, L, or Bloom (Allen et al., Environmental Microbiology, 9(4) 971-982 (2007)).

2. Marine Viruses

Marine viruses are the most abundant biological entities in the ocean. The impact of viral infection is enormous. By some estimates, viral infection of marine microorganisms eliminates 20% of the ocean's biomass per day. Thus, viruses may serve as a powerful ecological and evolutionary driving force for biodiversity in the ocean (Suttle, Nature Reviews Microbiology, Vol. 5, 801-812 (2007); Fuhrman, Nature 399:541-548 (1999)).

Viral killing of phytoplankton has been confirmed in laboratory experiments with lytic viruses, which direct phytoplankton hosts to produce progeny and eventually lyse the host to release progeny viruses. Studies suggest that the virus induces a cascade of metacaspase signaling, eventually leading to programmed cell death, which may act as a defense against massive viral infection and demise of the population. Activation of caspase-linked activity after viral infection has been identified in several phytoplankton species, including *E. huxleyi* (Bidle et al., PNAS 104(14): 6049-6054 (2007)).

Metacaspase genes or caspase-like homologues have also been identified in the genomes of many other marine algae, suggesting that viral induction of metacaspases and programmed cell death may be a conserved mechanism in phytoplankton (Bidle and Falkowski. Nature Rev. Microbiol. 2:643-655 (2004); Parker et al., Ann. Rev. Genet. 42:619-45 (2008)).

Marine viruses may be specific to the host phytoplankton. Accordingly, in one aspect of the present disclosure, the virus component in the virus-phytoplankton system is a Phycodnaviridae, a family that infects marine or freshwater eukaryotic algae. The virus may be a coccolithovirus (Wilson et al., Science, 309: 1090-1092 (2005)). The coccolithovirus may be EhV86, or other strains capable of infecting *E. huxleyi*. Suitable strains include EhV1, EhV-84, EhV-88, EhV-163, EhV-201, EhV-202, EhV-203, EhV-204, EhV-205, EhV-206, EhV-207, EhV-208, EhV-209, EhV-V2 (Allen et al., Environmental Microbiology, 9(4) 971-982 (2007)).

In the laboratory setting, viral particles are purified from a lysate of cells infected with the virus. For example, EhV86 may be first propagated by using batch cultures of *E. huxleyi* strain 374 (Ehux374) grown in f/2 (minus Si) at 18° C. in 14 hour: 10 hour light-dark illumination. Once clearing of the host cell culture is observed, virus-containing cell lysates are centrifuged and passed through 0.4 μm polycarbonate filters to remove cellular and particulate debris before infection. Viral lysates may be stored at 4° C. To infect fresh *E. huxleyi* cells, the viral lysates are added to exponentially growing ($1.5 \times 10^6$ mL$^{-1}$) cells. In some embodiments, 1 mL of lysate may be added to 100 mL of cells. Inoculated cultures may be occasionally agitated to encourage adsorption of virus to cells (Allen et al., Environmental Microbiology, 9(4): 971-982 (2007)). The latent period of a coccolithovirus in *E. huxleyi* is reported to be 12-14 hours, and burst size is 400-1000 infective units per cell (Brussard, J. Eukaryotic Microbiology, 51:2, 125-138, (2004))

*E. huxleyi* has been shown to carry virus-like particles of different size classes in one cell (Brussard, Aquat. Microb. Ecol., 10:105-113, (1996)). EhV86 is not known to infect species other than *E. huxleyi*, but other viruses are known to infect more than one phytoplankton: For example, *M. pusilla* can be infected by a dsDNA virus from the phycodnaviridae family and a dsRNA virus from the reoviridae family (Brussard, J. Eukaryot. Microbiol., 51(2), 125-138, (2004)). Any virus or combination of viruses that infect a phytoplankton of interest can be used in the methods disclosed herein.

B. Lipids

1. Induction of Sphingosine-Like Lipids and Glycerolipids

Following infection by virus, the phytoplankton may express viral gene products and/or express host gene products in response to the virus. Gene products may comprise nucleic acids such as DNA or RNA, amino acids, peptides, and/or proteins, any of which may be modified with lipids, sugars, phosphates or other moieties. By varying conditions of growth, such as light, temperature, time, and nutrients, the relative amounts and/or identities of the products generated may be varied.

In some embodiments, viruses induce production of lipids in the phytoplankton host. Expression of these lipids may occur immediately after infection by the virus, or may be observed within a range of 0.1-100 hours post-infection. In some embodiments, a new lipid may occur and/or may be observed at 1, 2 or 4 hours post-infection (Allen, J. Virology, 2006, 80(15) 7699-7705). In other embodiments, viral infection may induce a decrease in the levels of lipids, either viral lipids or host lipids. Thus, the levels of viral lipids, host lipids or a combination of both may increase or decrease over time and peak at or around 3.5 hours, 8 hours, 21 hours, 26.5 hours, 31.5 hours, 45 hours, 52 hours, 56 hours, 69 hours, 75.5 hours, 81.5 hours, and/or 92 hours.

Accordingly, in some embodiments of the present methods, aliquots of the cultures of virally-infected phytoplankton may be removed at intervals, a sample containing lipids may be extracted, and optionally one or more lipids may be further separated on the basis of size, mass, charge, polarity, or other physicochemical properties. The emergence or disappearance of lipids may be assayed at each time point. Molecules which increase or decrease over time may be viral-induced lipids—either of viral origin or host origin—which are suitable for bioactivity screens. Notably, lipids and/or other molecules may appear, disappear, or otherwise change over time in virus-sensitive strains, while corresponding lipids and/or other molecules do not appear, disappear, or otherwise change over time in virus-resistant strains. Comparing the lipid and/or molecule populations over time in virus-sensitive and virus-resistant strains may indicate that the lipids and/or molecules are associated with the virus infection.

In some embodiments, viruses induce production of sphingosine-like lipids in phytoplankton. Sphingolipids, a representative example of which is shown below, are a class of lipids derived from the aliphatic amino alcohol sphingosine.

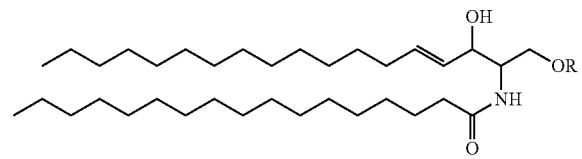

There are three main types of sphingolipids, differing in their head group R, which may be H, a sugar moiety, or another substituent. Sphingomyelins have a phosphorylcholine or phosphoroethanolamine molecule with an ether linkage to the 1-hydroxy group of a ceramide. Glycosylated sphingolipids are ceramides with one or more sugar residues joined in a β-glycosidic linkage at the 1-hydroxyl position. Cerebrosides have a single glucose or galactose at the 1-hydroxy position. Sulfatides are sulfated cerebrosides. Gangliosides have at least three sugars, one of which must be sialic acid. These compounds play important roles in signal transmission and cell recognition in many organisms. Sphingolipids may play a role in protecting cells by forming a mechanically stable and chemically resistant outer leaflet of the plasma membrane lipid bilayer. In addition, simple sphingolipid metabolites, such as ceramide and sphingosine-1-phosphate, have been shown to be important mediators in the signaling cascades involved in apoptosis, proliferation, and stress responses.

Sphingosine-like lipids, as the term is used herein, include sphingolipids as well as variant compounds in which either the fatty acid portion (i.e., corresponding to the C-17 unsaturated acyl group in the structure depicted above) or the sphingosine portion (i.e., corresponding to the unsaturated C-18 amino diol in the structure depicted above) is altered, e.g., by shortening or lengthening the alkyl chain, varying the number and/or position of unsaturated bonds, substituting the alkyl chain with substituents such as hydroxyl groups, etc., but generally share the overall structural characteristics of having a substantially linear polyol-amine chain in which the amine is acylated by a fatty acid. In certain embodiments, the sphingosine-like portion may be glycosylated, e.g., with one or more sugar residues, such as a glucose or galactose residue, as is commonly seen in cerebrosides, or may be unglycosylated, e.g., bearing an unmodified primary alcohol (e.g., corresponding to R=H in the structure depicted above).

Notably, viruses contain homologues to sphingolipid genes. In the coccolithovirus EhV86, there are at least four genes involved in sphingolipid biosynthesis, encoding sterol desaturase, serine palmitoyltransferase, transmembrane fatty acid elongation protein, lipid phosphate phosphatase, and a two additional genes encoding desaturases (Wilson et al., Science 209, 1090 (2005)). Without wishing to be bound by any theory, in one model of virus-phytoplankton interaction, viral sphingosine-like lipids induce apoptosis in infected phytoplankton.

Consistent with this hypothesis, novel polar membrane lipids appear and increase after viral infection of E. huxleyi. As disclosed herein, the lipids are glycosylated sphingosine-like lipids, and yield fragmentation ions that indicate an origin from the intermediate compound myristoyl-CoA. This origin is consistent with viral-directed synthesis of glycosylated sphingosine-like lipids, as the host phytoplankton produce palmitoyl glycosylated sphingosine-like lipids. Notably, the myristoyl GSLs are present in infected, virus-sensitive strains, but not in virus-resistant strains.

In certain embodiments, a group of glycerolipids is produced after viral infection of phytoplankton. In certain such embodiments, these glycerolipids (herein called 802 lipids) increase concomitantly with a decrease in a second group of glycerolipids (herein called the 830 lipids). The 802 lipids, when isolated and added to a culture of newly-infected phytoplankton, lead to prolonged survival of virus-infected cells. Glycerolipids, like sphingosine-like lipids, are second messengers that may be involved in signaling cascades involving apoptosis, proliferation, and stress responses.

2. Isolation of Lipids

As described above, lipids may be extracted and monitored over the course of viral infection. Changes in lipid dynamics, such as the emergence of new sphingosine-like lipids, can be observed by isolating lipids or pools of lipids within a sample. Such lipids may be extracted using a Bligh-Dyer method, or a variation thereof, such that all lipids in a phytoplankton cell lysate are extracted in solvents methanol, dichloromethane, and phosphate buffer. Then, the extracted lipid sample may be further separated by chromatography, such as high performance liquid chromatography (HPLC), in order to separate lipids (or pools of lipids) according to their hydrophobicity, size, charge, solubility in a given solvent, adsorption onto stationary phase, and/or other structural properties. Mass spectrometry (MS) analysis may also be used to elucidate the structure and chemical properties of unknown compounds. Thus, for a collection of lipid samples gathered over the time course of viral infection, a lipid profile may be generated, wherein levels of lipids or groups of lipids are monitored. As described above, the lipid profile may change over time, and new lipids, such as sphingosine-like lipids or glycerolipids, may be identified.

2a. Exemplary Lipids

Figure 8:
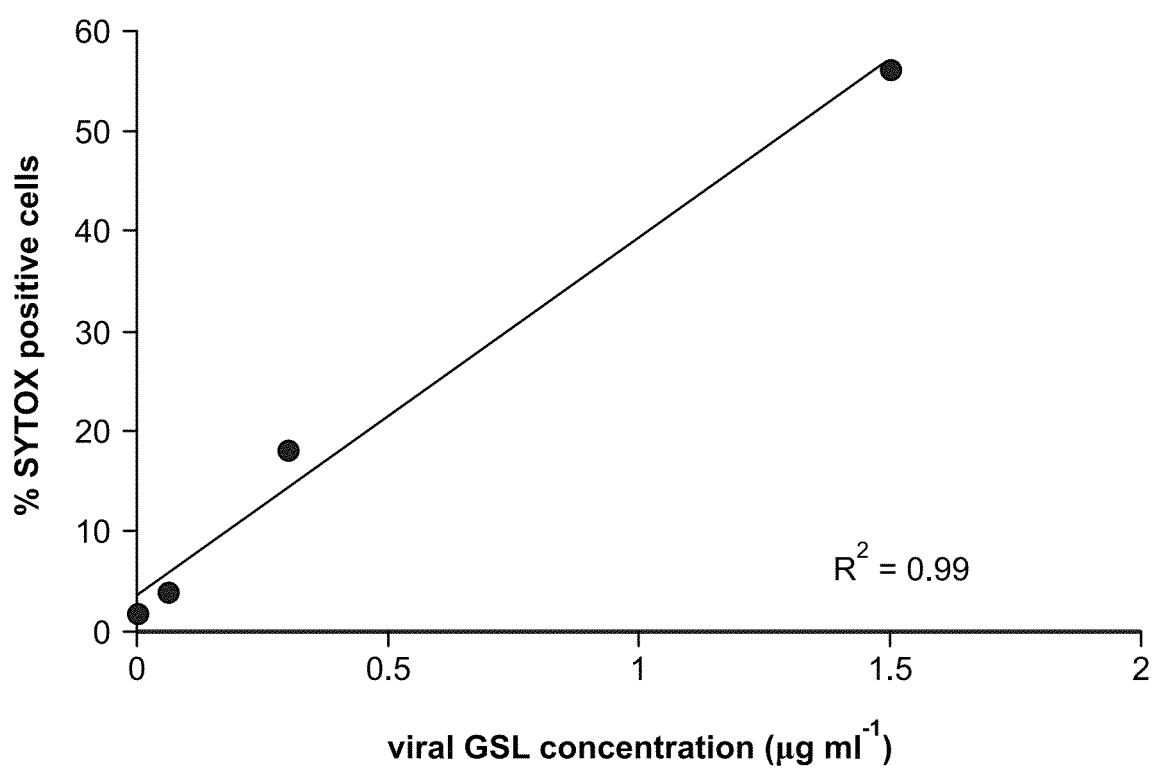
FIG. 8 shows the linear regression between the applied, viral GSL concentration and cell death, taken as the percentage of SYTOX positive cells. An effective, threshold viral GSL concentration of 0.2 µg $ml^{-1}$ was extrapolated to induce PCD and cell lysis. This is the viral GSL concentration required for >10% SYTOX positive cells. Data corresponds to that presented in FIG. 3.

Using HPLC, sphingosine-like lipids can be isolated from Ehux 374 infected with EhV86, and tested for ability to modulate apoptosis. In some embodiments, specific compounds may be isolated. These compounds, as well as their analogs and derivatives, can be used in the compositions and methods disclosed herein. In some embodiments, the lipids may be characterized as having a mass spectra pattern substantially the same as that shown in FIG. 8 and/or 9.

In certain embodiments, the compound has a structure of formula (I)

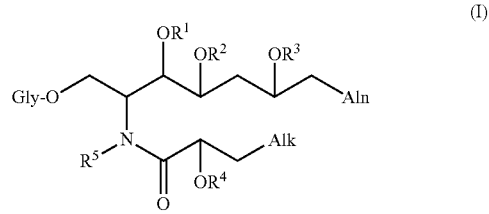

or a pharmaceutically acceptable salt thereof, wherein

Gly is a glycosidic residue;

$R^1$, $R^2$, $R^3$, $R^4$ and $R^5$ are each independently selected from hydrogen, $C_{1-6}$alkyl, and $C_{1-6}$alkylcarbonyl, preferably hydrogen;

Aln is a $C_{2-25}$alkenyl group; and

Alk is a $C_{1-25}$alkyl group.

In certain embodiments, Gly is a monosaccharide selected from a pentose and a hexose, preferably a hexose. In certain embodiments, Gly is a pentose selected from ribose, arabinose, xylose, and lyxose. In certain preferred embodiments, Gly is a hexose selected from allose, altrose, glucose, mannose, gulose, idose, galactose, and tallose. In certain embodiments, Gly is an amino glycoside. In certain such embodiments, Gly is selected from galactosamine, glucosamine, and sialic acid. In certain embodiments, Gly represents a modified monosaccharide, e.g., in which one or more of the hydroxyls is alkylated or esterified.

In certain embodiments, Gly has a structure

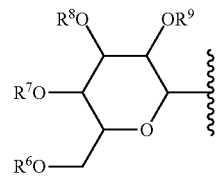

wherein $R^6$, $R^7$, $R^8$, and $R^9$ are each independently selected from hydrogen, $C_{1-6}$alkyl, and $C_{1-6}$alkylcarbonyl, preferably hydrogen.

In certain embodiments, Gly is a sugar moiety having a D-stereochemical configuration. In certain alternative embodiments, Gly is a sugar moiety having an L-stereochemical configuration. In certain embodiments, Gly is an α-glycosidic moiety. In certain alternative embodiments, Gly is a β-glycosidic moiety.

In certain embodiments, Gly is an oligosaccharide or polysaccharide, e.g., comprising two or more of the above-described monosaccharides in sequence.

In certain embodiments, Aln is $C_{2-25}$alkenyl comprising at least one unsaturation. In certain preferred embodiments, Aln comprises 1 to 3 unsaturations, preferably one unsaturation. In certain embodiments, Aln is a $C_{5-15}$alkenyl, preferably a $C_{6-14}$alkenyl, a $C_{7-13}$alkenyl, or a $C_{8-12}$alkenyl. In certain preferred embodiments, Aln is a $C_8$alkenyl, $C_9$alkenyl, or a $C_{10}$alkenyl, e.g.,

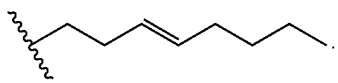 [SMILES: *CC/C=C/CCCC]

In certain embodiments, Alk is a $C_{1-25}$alkyl, preferably $C_{10-20}$alkyl. In certain embodiments, Alk is a $C_{10}$alkyl, $C_{11}$alkyl, $C_{12}$alkyl, $C_{13}$alkyl, $C_{14}$alkyl, or a $C_{15}$alkyl. In certain preferred embodiments, Alk is a $C_{14}$alkyl.

In certain preferred embodiments, a compound of Formula (I) is

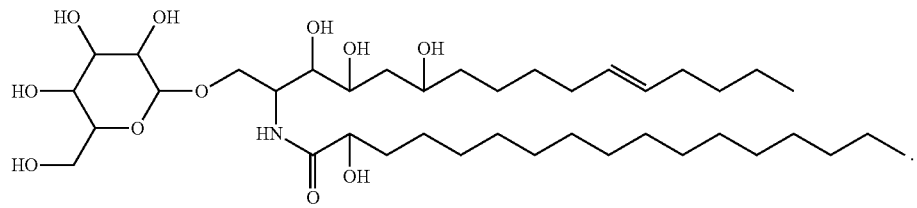 [SMILES: CCCC/C=C/CCCCC(O)CC(O)C(O)C(COC1OC(CO)C(O)C(O)C1O)NC(=O)C(O)CCCCCCCCCCCCCCC]

In certain alternative embodiments, a compound of Formula (I) is not

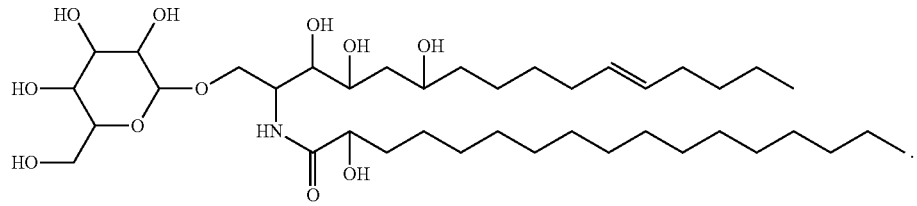 [SMILES: CCCC/C=C/CCCCC(O)CC(O)C(O)C(COC1OC(CO)C(O)C(O)C1O)NC(=O)C(O)CCCCCCCCCCCCCCC]

In certain embodiments, the invention relates to prodrugs of compounds disclosed herein. The term "prodrug" encompasses compounds that, under physiological conditions, are converted into therapeutically active agents. A common method for making a prodrug is to include selected moieties that are hydrolyzed under physiological conditions to reveal the desired molecule. In other embodiments, the prodrug is converted by an enzymatic activity of the host animal.

The term "alkyl" refers to substituted or unsubstituted saturated hydrocarbon groups, including straight-chain alkyl and branched-chain alkyl groups. Accordingly, the term "$C_{x-y}$alkyl" refers to an alkyl that contain from x to y carbons in the chain, including haloalkyl groups such as trifluoromethyl and 2,2,2-trifluoroethyl, etc. The terms "alkenyl" and "alkynyl" refer to substituted or unsubstituted unsaturated aliphatic groups analogous in length and possible substitution to the alkyls described above, but that contain at least one double or triple bond respectively.

The term "carbonyl" is art-recognized and includes such moieties as can be represented by the general formula:

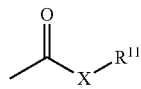

wherein X is a bond or represents an oxygen or a sulfur, and $R^{11}$ represents a hydrogen, an alkyl, an alkenyl, —$(CH_2)_m$—$R^8$ or a pharmaceutically acceptable salt. Where X is an oxygen and $R^{11}$ is not hydrogen, the formula represents an "ester". Where X is an oxygen, and $R^{11}$ is a hydrogen, the formula represents a "carboxylic acid".

The term "hydrocarbon", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to aryl, heteroaryl, carbocycle, heterocycle, alkyl, alkenyl, alkynyl, and combinations thereof.

The term "preventing" is art-recognized, and when used in relation to a condition, such as a local recurrence (e.g., pain), a disease such as cancer, a syndrome complex such as heart failure or any other medical condition, is well understood in the art, and includes administration of a composition which reduces the frequency of, or delays the onset of, symptoms of a medical condition in a subject relative to a subject which does not receive the composition. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount. Prevention of an infection includes, for example, reducing the number of diagnoses of the infection in a treated population versus an untreated control population, and/or delaying the onset of symptoms of the infection in a treated population versus an untreated control population. Prevention of pain includes, for example, reducing the magnitude of, or alternatively delaying, pain sensations experienced by subjects in a treated population versus an untreated control population.

The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic, (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof).

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate.

As used herein, the term "treating" or "treatment" includes reversing, reducing, or arresting the symptoms, clinical signs, and underlying pathology of a condition in manner to improve or stabilize a subject's condition.

3. Screening of Lipids for Apoptosis-Inducing Activity

Initially, an isolated fraction containing a sphingosine-like lipid or glycerolipid may be tested for bioactivity, such as apoptosis-associated activity. Apoptosis, the process of programmed cell death (PCD), or cell suicide, is a response to inductive signals originating either external or internal to the cell, which trigger an organized cascade of biochemical and cellular changes. Apoptosis-associated activity comprises one or more of these changes, such as apoptosis, cell shrinkage, blebbing of cell membranes, chromatin condensation and fragmentation, formation of apoptotic bodies, expression of caspase genes, increase in caspase activity, and/or expression of genes associated with apoptosis.

In some embodiments, target cells are contacted with fractions containing lipids, such as sphingosine-like lipids, and apoptosis-associated activity is measured. In other embodiments, target cells are contacted with fractions containing lipids, such as glycerolipids, in the presence of a stimulus that induces apoptosis in untreated cells (such as an apoptosis-inducing virus), and inhibition of apoptosis-associated activity is measured. Detection of apoptosis-associated activity may rely on direct observation of morphological changes in cells. Detection may be performed by microscopic, fluorescence-based and biochemical procedures. Electron microscopy and phase contrast microscopy, for example, detect the morphological appearance during apoptosis, such as shrinkage, membrane protuberances, and the presence of micronuclei (Verhaegen et al., European Microscopy and Analysis (1998)).

In other embodiments, apoptosis-associated activity in test cells contacted with lipids is detected in a flow cytometer. Detection of apoptosis in a sample of suspended cells can be performed using a flow cytometer. Here, fluorescence dyes staining DNA are used (Elstein and Zucker, Experimental Cell Research 211, 322-331 (1994)), or a biochemical method is employed in which the process of DNA fragmentation is visualized by incorporation of nucleotides with fluorescent labels (e.g., TUNEL method, Douglas et al., Journal of Immunological Methods 188, 219-228 (1995)). Also, specific fluorescently labelled probes can be used for cell surface molecules. An example of such a probe is fluorescently labelled annexin V (Koopman et al., Blood 84, 5, 1415-1420 (1994)) which binds to phosphatidylserine on the cell surface and thus visualizes the restructuring of the plasma membrane in the early apoptotic stage. Lastly, one can detect the in vivo activation of caspases, a class of proteases that initiate and execute PCD, through the staining of cells with a fluorescently-labeled (FITC) broad spectrum caspsae inhibitor (z-VAD-FMK). (Bidle and Bender, Eukaryotic Cell 7:223-236 (2008); Bidle et al., Proc. Natl. Acad. Sci. USA 104: 6049-6054 (2007)). However, flow-cytometric methods for the measurement of apoptosis typically require calibration of the method and the system. In addition, a high number of cells (approx. $10^6$) is beneficial for analysis.

Other methods for the detection of apoptosis may require the destruction of all test cells in a sample and the gel-electrophoretic or biochemical detection of DNA fragmentation (Leist et al., The Journal of Immunology 153, 1778-1788 (1994)). These biochemical methods are procedures with several steps in which several reagents are used. This results in a very long time of analysis of up to 6 hours. In addition, several hundred cells are typically used for one analysis.

Detection of apoptosis may also depend on indirect measurements, such as photosynthetic efficiency in phytoplankton. Phytoplankton undergoing apoptosis show a marked reduction in photosynthetic efficiency.

In some embodiments, screens for apoptosis-associated activity may be performed in cell-based assays. The use of genetically-engineered cells, including bacteria, fungi, insect, marine microorganisms, plant cells, and animal cells, is also amenable to high throughput screening (HTS) and automated protocols. Cell-based assays may require that a test compound modulate the expression, binding or activity of a target inside the cell, in such a way that changes to the target are measurable.

In some embodiments, the target cells used in an assay system come from the organism(s) in which a bioactive compound will be used. Thus, target cells may be prokaryotic cells or eukaryotic cells. Cells may be phytoplankton cells, e.g., coccolithophores, such as E. huxleyi. Cells may also be plant or animal cells, such as mammalian cells. Cells may be human cells. In some embodiments, cells may be genetically altered to trigger a specific output (e.g., a fluorescent signal) in the presence of a bioactive compound.

4. Apoptosis in Target Cells

Lipids which induce apoptosis in target cells may prove useful in a variety of settings. In some embodiments, target cells belong to organisms that attach to a surface in contact with water for a period of time. For example, apoptosis-inducing lipids identified using the present methods may be used to induce apoptosis in barnacles, in order to prevent the growth of barnacles on the hulls and/or heating/cooling systems of ships, fishing equipment, and/or offshore oil and gas rigs. Similarly, such lipids may be used to induce apoptosis in algae, diatoms such as *Achnanthes* or *Stauronesis* or bacteria such as *Thiobacilli*, which form a biofilm on surfaces. Biofilms may provide a foundation for growth of seaweed, barnacles, mollusks, seasquirts, sponges, sea anenomes, bryzoans, tube worms, polychaetes, etc. Apoptosis-inducing lipids may be also used to induce apoptosis in any such macroorganisms.

Lipids, such as sphingosine-like lipids identified by the present methods may also be used to induce apoptosis in plant cells. Sphingosine-like lipids such as ceramide are thought to modulates apoptosis in plants (Khuruna et al., Current Science, 88 (5) 740-752 (2005)). Accordingly, sphingosine-like lipids may be screened for apoptosis-inducing activity in specific target plants. For example, a sphingosine-like lipid may be used to kill weeds while leaving crops intact.

Defects in apoptosis form the basis for many diseases in animals. Many cancers, including colorectal cancer, glioma, hepatic cancer, neuroblastoma, leukemias and lymphomata, and prostate cancer have been associated with defects in apoptosis. Autoimmune diseases such as myasthenia gravis and systemic lupus erythematosus, as well as inflammatory diseases such as bronchial asthma, inflammatory intestinal disease, and pulmonary inflammation are also associated with failure of specific immune cells to undergo apoptosis. Finally, some viruses such as HSV, respiratory syncytial virus, HCV, and others may inhibit apoptosis of infected cells. Accordingly, apoptosis-inducing sphingosine-like lipids identified using the present methods may be used to induce apoptosis in cancer cells, lymphocytes that recognize self-peptides, virally-infected cells, or any other cells whose defective apoptosis leads to or contributes to a disease condition.

Similarly, apoptosis-inhibiting lipids identified using the present methods may be used to promote resistance to viral-induced apoptosis. Many viruses, such as dengue virus, EBV, HIV, varicella zoster virus, Abelson virus, are known to promote apoptosis or encode proteins that promote apoptosis. Mechanisms controlling viral-induced apoptosis may be the same mechanisms that are affected in diseases associated with excess apoptosis. Examples of such diseases include, but are not limited to, AIDS, Alzheimer's Disease, ALS, Parkinson's Disease, retinitis pigmentosa, epilepsy, aplastic anemia, myelodysplastic syndrome, lymphocytopenia. Thus, the glycerolipids identified using the present methods may be used to promote resistance to viral-induced apoptosis, or for treating diseases associated with excess apoptosis.

5. Cancer and Combination Therapies

In certain embodiments, compounds of the invention, such as sphingosine-like lipids, may be used to treat or prevent cancer in an individual. The terms "cancer," "tumor," and "neoplasia" are used interchangeably herein. As used herein, a cancer (tumor or neoplasia) is characterized by one or more of the following properties: cell growth is not regulated by the normal biochemical and physical influences in the environment; anaplasia (e.g., lack of normal coordinated cell differentiation); and in some instances, metastasis. Cancer diseases include, for example, anal carcinoma, bladder carcinoma, breast carcinoma, cervical carcinoma, chronic lymphocytic leukemia, chronic myelogenous leukemia, endometrial carcinoma, hairy cell leukemia, head and neck carcinoma, lung (small cell) carcinoma, multiple myeloma, non-Hodgkin's lymphoma, follicular lymphoma, ovarian carcinoma, brain tumors, colorectal carcinoma, hepatocellular carcinoma, Kaposi's sarcoma, lung (non-small cell carcinoma), melanoma, pancreatic carcinoma, prostate carcinoma, renal cell carcinoma, and soft tissue sarcoma. Additional cancer disorders can be found in, for example, Isselbacher et al. (1994) Harrison's Principles of Internal Medicine 1814-1877, herein incorporated by reference.

In a related embodiment, compounds of the invention may be used in conjunction with other anti-tumor therapies such as conventional chemotherapy directed against solid tumors and for control of establishment of metastases. The administration of the other anti-tumor therapies can be conducted during or after chemotherapy. Such agents are typically formulated with a pharmaceutically acceptable carrier, and can be administered intravenously, orally, bucally, parenterally, by an inhalation spray, by topical application or transdermally. An agent can also be administered by local administration. Preferably, one or more additional agents administered in conjunction with an anti-cancer chemotherapeutic agent (e.g., a compound of the invention) inhibits cancer cells in an additive or synergistic manner compare.

A wide array of conventional compounds has been shown to have anti-tumor activities. These compounds have been used as pharmaceutical agents in chemotherapy to shrink solid tumors, prevent metastases and further growth, or decrease the number of malignant cells in leukemic or bone marrow malignancies. Although chemotherapy has been effective in treating various types of malignancies, many anti-tumor compounds induce undesirable side effects. In many cases, when two or more different treatments are combined, the treatments may work synergistically and allow reduction of dosage of each of the treatments, thereby reducing the detrimental side effects exerted by each compound at higher dosages. In other instances, malignancies that are refractory to a treatment may respond to a combination therapy of two or more different treatments.

Therefore, compounds of the present invention may be conjointly administered with a conventional anti-tumor compound. Conventional anti-tumor compounds include, merely to illustrate: aminoglutethimide, amsacrine, anastrozole, asparaginase, bcg, bicalutamide, bleomycin, buserelin, busulfan, camptothecin, capecitabine, carboplatin, carmustine, chlorambucil, cisplatin, cladribine, clodronate, colchicine, cyclophosphamide, cyproterone, cytarabine, dacarbazine, dactinomycin, daunorubicin, dienestrol, diethylstilbestrol, docetaxel, doxorubicin, epirubicin, estradiol, estramustine, etoposide, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, ironotecan, letrozole, leucovorin, leuprolide, levamisole, lomustine, mechlorethamine, medroxyprogesterone, megestrol, melphalan, mercaptopurine, mesna, methotrexate, mitomycin, mitotane, mitoxantrone, nilutamide, nocodazole, octreotide, oxaliplatin, paclitaxel, pamidronate, pentostatin, plicamycin, porfimer, procarbazine, raltitrexed, rituximab, streptozocin, suramin, tamoxifen, temozolomide, teniposide, testosterone, thioguanine, thiotepa, titanocene dichloride, topotecan, trastuzumab, tretinoin, vinblastine, vincristine, vindesine, and vinorelbine.

In other embodiments, compounds of the invention may be conjointly administered with a conventional anti-tumor compound selected from: an EGF-receptor antagonist, arsenic sulfide, adriamycin, cisplatin, carboplatin, cimetidine, caminomycin, mechlorethamine hydrochloride, pentamethylmelamine, thiotepa, teniposide, cyclophosphamide, chlorambucil, demethoxyhypocrellin A, melphalan, ifosfamide, trofosfamide, Treosulfan, podophyllotoxin or podophyllotoxin derivatives, etoposide phosphate, teniposide, etoposide, leurosidine, leurosine, vindesine, 9-aminocamptothecin, camptoirinotecan, crisnatol, megestrol, methopterin, mitomycin C, ecteinascidin 743, busulfan, carmustine (BCNU), lomustine (CCNU), lovastatin, 1-methyl-4-phenylpyridinium ion, semustine, staurosporine, streptozocin, phthalocyanine, dacarbazine, aminopterin, methotrexate, trimetrexate, thioguanine, mercaptopurine, fludarabine, pentastatin, cladribin, cytarabine (ara C), porfiromycin, 5-fluorouracil, 6-mercaptopurine, doxorubicin hydrochloride, leucovorin, mycophenolic acid, daunorubicin, deferoxamine, floxuridine, doxifluridine, raltitrexed, idarubicin, epirubican, pirarubican, zorubicin, mitoxantrone, bleomycin sulfate, actinomycin D, safracins, saframycins, quinocarcins, discodermolides, vincristine, vinblastine, vinorelbine tartrate, vertoporfin, paclitaxel, tamoxifen, raloxifene, tiazofuran, thioguanine, ribavirin, EICAR, estramustine, estramustine phosphate sodium, flutamide, bicalutamide, buserelin, leuprolide, pteridines, enediynes, levamisole, aflacon, interferon, interleukins, aldesleukin, filgrastim, sargramostim, rituximab, BCG, tretinoin, betamethosone, gemcitabine hydrochloride, verapamil, VP-16, altretamine, thapsigargin, oxaliplatin, iproplatin, tetraplatin, lobaplatin, DCP, PLD-147, JM118, JM216, JM335, satraplatin, docetaxel, deoxygenated paclitaxel, TL-139, 5'-nor-anhydrovinblastine (hereinafter: 5'-nor-vinblastine), camptothecin, irinotecan (Camptosar, CPT-11), topotecan (Hycamptin), BAY 38-3441, 9-nitrocamptothecin (Orethecin, rubitecan), exatecan (DX-8951), lurtotecan (GI-147211C), gimatecan, homocamptothecins diflomotecan (BN-80915) and 9-aminocamptothecin (IDEC-13'), SN-38, ST1481, karanitecin (BNP1350), indolocarbazoles (e.g., NB-506), protoberberines, intoplicines, idenoisoquinolones, benzo-phenazines or NB-506.

In another related embodiment, compounds of the invention may be used in conjunction with other anti-tumor therapies such as radiation. As used herein, the term "radiation" is intended to include any treatment of a neoplastic cell or subject by photons, neutrons, electrons, or other type of ionizing radiation. Such radiations include, but are not limited to, X-ray, gamma-radiation, or heavy ion particles, such as alpha or beta particles. Additionally, the radiation may be radioactive. The means for irradiating neoplastic cells in a subject are well known in the art and include, for example, external beam therapy, and brachytherapy.

Methods to determine if a cancer (tumor or neoplasia) has been treated are well known to those skilled in the art and include, for example, a decrease in the number of tumor cells (e.g., a decrease in cell proliferation or a decrease in tumor size). It is recognized that the treatment of the present invention may be a lasting and complete response or can encompass a partial or transient clinical response. See for example, Isselbacher et al. (1996) Harrison's Principles of Internal Medicine 13 ed., 1814-1882, incorporated herein by reference.

Assays to test for the sensitization or the enhanced death of tumor cells are well known in the art, including, for example, standard dose response assays that assess cell viability; agarose gel electrophoresis of DNA extractions or flow cytometry to determine DNA fragmentation, a characteristic of cell death; assays that measure the activity of polypeptides involved in apoptosis; and assay for morphological signs of cell death. The details regarding such assays are described elsewhere herein. Other assays include, chromatin assays (e.g., counting the frequency of condensed nuclear chromatin) or drug resistance assays as described in, for example, Lowe et al. (1993) Cell 74:95 7-697, herein incorporated by reference. See also U.S. Pat. No. 5,821,072, also herein incorporated by reference.

5. Administration

Compounds prepared as described herein can be administered in various forms, depending on the disorder to be treated and the age, condition, and body weight of the patient, as is well known in the art. For example, where the compounds are to be administered orally, they may be formulated as tablets, capsules, granules, powders, or syrups; or for parenteral administration, they may be formulated as injections (intravenous, intramuscular, or subcutaneous), drop infusion preparations, or suppositories. For application by the ophthalmic mucous membrane route, they may be formulated as eye drops or eye ointments. These formulations can be prepared by conventional means, and if desired, the active ingredient may be mixed with any conventional additive or excipient, such as a binder, a disintegrating agent, a lubricant, a corrigent, a solubilizing agent, a suspension aid, an emulsifying agent, a coating agent, a cyclodextrin, and/or a buffer. Although the dosage will vary depending on the symptoms, age and body weight of the patient, the nature and severity of the disorder to be treated or prevented, the route of administration and the form of the drug, in general, a daily dosage of from 0.01 to 2000 mg of the compound is recommended for an adult human patient, and this may be administered in a single dose or in divided doses. The amount of active ingredient which can be combined with a carrier material to produce a single dosage form will generally be that amount of the compound which produces a therapeutic effect.

The precise time of administration and/or amount of the composition that will yield the most effective results in terms of efficacy of treatment in a given patient will depend upon the activity, pharmacokinetics, and bioavailability of a particular compound, physiological condition of the patient (including age, sex, disease type and stage, general physical condition, responsiveness to a given dosage, and type of medication), route of administration, etc. However, the above guidelines can be used as the basis for fine-tuning the treatment, e.g., determining the optimum time and/or amount of administration, which will require no more than routine experimentation consisting of monitoring the subject and adjusting the dosage and/or timing.

The phrase "pharmaceutically acceptable" is employed herein to refer to those ligands, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition, or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose, and sucrose; (2) starches, such as corn starch, potato starch, and substituted or unsubstituted β-cyclodextrin; (3) cellulose, and its derivatives, such as sodium carboxymethyl cellulose, ethyl cellulose, and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil, and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations. In certain embodiments, pharmaceutical compositions of the present invention are non-pyrogenic, i.e., do not induce significant temperature elevations when administered to a patient.

The term "pharmaceutically acceptable salt" refers to the relatively non-toxic, inorganic and organic acid addition salts of the compound(s). These salts can be prepared in situ during the final isolation and purification of the compound(s), or by separately reacting a purified compound(s) in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, laurylsulphonate salts, and amino acid salts, and the like. (See, for example, Berge et al. "Pharmaceutical Salts", *J. Pharm. Sci.* 66: 1-19.)

In other cases, the compounds useful in the methods of the present invention may contain one or more acidic functional groups and, thus, are capable of forming pharmaceutically acceptable salts with pharmaceutically acceptable bases. The term "pharmaceutically acceptable salts" in these instances refers to the relatively non-toxic inorganic and organic base addition salts of a compound(s). These salts can likewise be prepared in situ during the final isolation and purification of the compound(s), or by separately reacting the purified compound(s) in its free acid form with a suitable base, such as the hydroxide, carbonate, or bicarbonate of a pharmaceutically acceptable metal cation, with ammonia, or with a pharmaceutically acceptable organic primary, secondary, or tertiary amine. Representative alkali or alkaline earth salts include the lithium, sodium, potassium, calcium, magnesium, and aluminum salts, and the like. Representative organic amines useful for the formation of base addition salts include ethylamine, diethylamine, ethylenediamine, ethanolamine, diethanolamine, piperazine, and the like (see, for example, Berge et al., supra).

Wetting agents, emulsifiers, and lubricants, such as sodium lauryl sulfate and magnesium stearate, as well as coloring agents, release agents, coating agents, sweetening, flavoring, and perfuming agents, preservatives and antioxidants can also be present in the compositions.

Examples of pharmaceutically acceptable antioxidants include: (1) water soluble antioxidants, such as ascorbic acid, cysteine hydrochloride, sodium bisulfate, sodium metabisulfite, sodium sulfite, and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations suitable for oral administration may be in the form of capsules, cachets, pills, tablets, lozenges (using a flavored basis, usually sucrose and acacia or tragacanth), powders, granules, or as a solution or a suspension in an aqueous or nonaqueous liquid, or as an oil-in-water or water-in-oil liquid emulsion, or as an elixir or syrup, or as pastilles (using an inert matrix, such as gelatin and glycerin, or sucrose and acacia) and/or as mouthwashes, and the like, each containing a predetermined amount of a compound(s) as an active ingredient. A composition may also be administered as a bolus, electuary, or paste.

In solid dosage forms for oral administration (capsules, tablets, pills, dragees, powders, granules, and the like), the active ingredient is mixed with one or more pharmaceutically acceptable carriers, such as sodium citrate or dicalcium phosphate, and/or any of the following: (1) fillers or extenders, such as starches, cyclodextrins, lactose, sucrose, glucose, mannitol, and/or silicic acid; (2) binders, such as, for example, carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets, and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols, and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound(s) moistened with an inert liquid diluent.

Tablets, and other solid dosage forms, such as dragees, capsules, pills, and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes, and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration include pharmaceutically acceptable emulsions, microemulsions, solutions, suspensions, syrups, and elixirs. In addition to the active ingredient, the liquid dosage forms may contain inert diluents commonly used in the art, such as, for example, water or other solvents, solubilizing agents, and emulsifiers such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols, and fatty acid esters of sorbitan, and mixtures thereof.

Besides inert diluents, the oral compositions can also include adjuvants such as wetting agents, emulsifying and suspending agents, sweetening, flavoring, coloring, perfuming, and preservative agents.

Suspensions, in addition to the active compound(s) may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing one or more compound(s) with one or more suitable nonirritating excipients or carriers comprising, for example, cocoa butter, polyethylene glycol, a suppository wax or a salicylate, which is solid at room temperature, but liquid at body temperature and, therefore, will melt in the rectum or vaginal cavity and release the active agent.

Formulations which are suitable for vaginal administration also include pessaries, tampons, creams, gels, pastes, foams, or spray formulations containing such carriers as are known in the art to be appropriate.

Dosage forms for the topical or transdermal administration of a compound(s) include powders, sprays, ointments, pastes, creams, lotions, gels, solutions, patches, and inhalants. The active component may be mixed under sterile conditions with a pharmaceutically acceptable carrier, and with any preservatives, buffers, or propellants which may be required.

The ointments, pastes, creams, and gels may contain, in addition to compound(s), excipients, such as animal and vegetable fats, oils, waxes, paraffins, starch, tragacanth, cellulose derivatives, polyethylene glycols, silicones, bentonites, silicic acid, talc, and zinc oxide, or mixtures thereof.

Powders and sprays can contain, in addition to a compound(s), excipients such as lactose, talc, silicic acid, aluminum hydroxide, calcium silicates, and polyamide powder, or mixtures of these substances. Sprays can additionally contain customary propellants, such as chlorofluorohydrocarbons and volatile unsubstituted hydrocarbons, such as butane and propane.

The compound(s) can be alternatively administered by aerosol. This is accomplished by preparing an aqueous aerosol, liposomal preparation, or solid particles containing the composition. A nonaqueous (e.g., fluorocarbon propellant) suspension could be used. Sonic nebulizers are preferred because they minimize exposing the agent to shear, which can result in degradation of the compound.

Ordinarily, an aqueous aerosol is made by formulating an aqueous solution or suspension of the agent together with conventional pharmaceutically acceptable carriers and stabilizers. The carriers and stabilizers vary with the requirements of the particular composition, but typically include nonionic surfactants (Tweens, Pluronics, sorbitan esters, lecithin, Cremophors), pharmaceutically acceptable co-solvents such as polyethylene glycol, innocuous proteins like serum albumin, oleic acid, amino acids such as glycine, buffers, salts, sugars, or sugar alcohols. Aerosols generally are prepared from isotonic solutions.

Transdermal patches have the added advantage of providing controlled delivery of a compound(s) to the body. Such dosage forms can be made by dissolving or dispersing the agent in the proper medium. Absorption enhancers can also be used to increase the flux of the compound(s) across the skin. The rate of such flux can be controlled by either providing a rate controlling membrane or dispersing the compound(s) in a polymer matrix or gel.

Pharmaceutical compositions of this invention suitable for parenteral administration comprise one or more compound(s) in combination with one or more pharmaceutically acceptable sterile aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include tonicity-adjusting agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. For example, delayed absorption of a parenterally administered drug form is accomplished by dissolving or suspending the drug in an oil vehicle.

Injectable depot forms are made by forming microencapsule matrices of compound(s) in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

The preparations of agents may be given orally, parenterally, topically, or rectally. They are, of course, given by forms suitable for each administration route. For example, they are administered in tablets or capsule form, by injection, inhalation, eye lotion, ointment, suppository, infusion; topically by lotion or ointment; and rectally by suppositories. Oral administration is preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection, and infusion.

The phrases "systemic administration," "administered systemically," "peripheral administration" and "administered peripherally" as used herein mean the administration of a ligand, drug, or other material other than directly into the central nervous system, such that it enters the patient's system and thus, is subject to metabolism and other like processes, for example, subcutaneous administration.

These compound(s) may be administered to humans and other animals for therapy by any suitable route of administration, including orally, nasally, as by, for example, a spray, rectally, intravaginally, parenterally, intracisternally, and topically, as by powders, ointments or drops, including buccally and sublingually.

Regardless of the route of administration selected, the compound(s), which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The concentration of a disclosed compound in a pharmaceutically acceptable mixture will vary depending on several factors, including the dosage of the compound to be administered, the pharmacokinetic characteristics of the compound(s) employed, and the route of administration. In general, the compositions of this invention may be provided in an aqueous solution containing about 0.1-10% w/v of a compound disclosed herein, among other substances, for parenteral administration. Typical dose ranges are from about 0.01 to about 50 mg/kg of body weight per day, given in 1-4 divided doses. Each divided dose may contain the same or different compounds of the invention. The dosage will be an effective amount depending on several factors including the overall health of a patient, and the formulation and route of administration of the selected compound(s).

EXAMPLES

The invention now being generally described, it will be more readily understood by reference to the following examples, which are included merely for purposes of illustration of certain embodiments and embodiments of the present invention, and are not intended to limit the invention.

Example 1

Figure 1B:
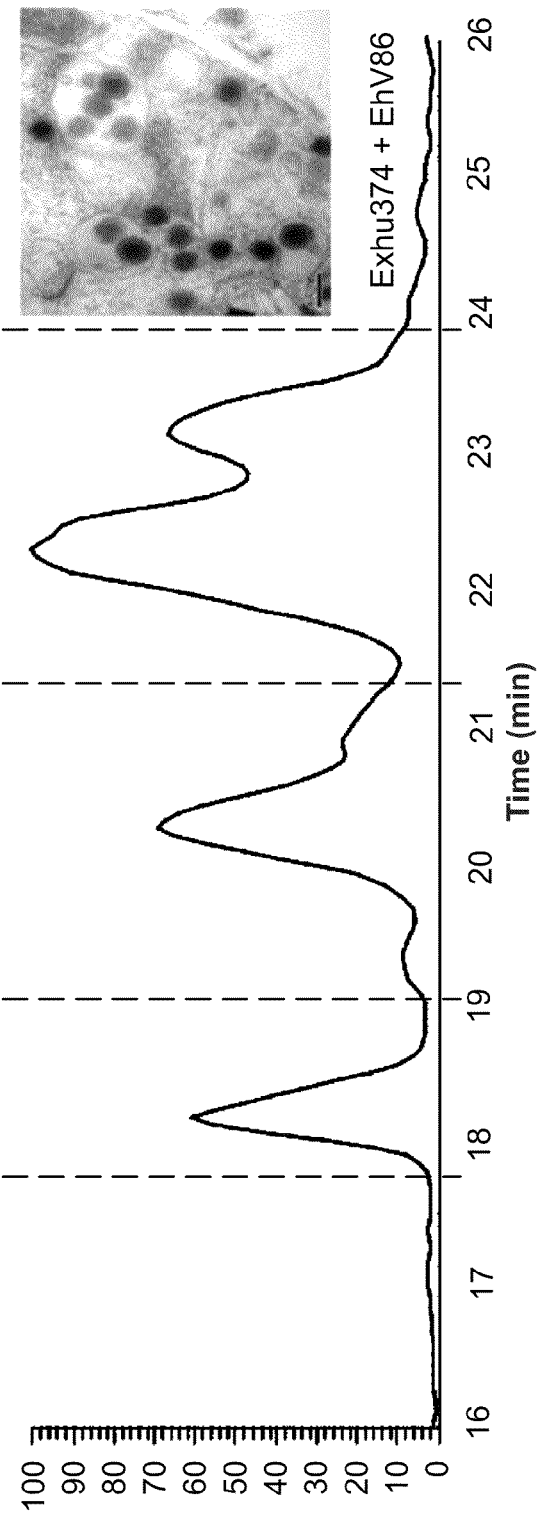

Polar Membrane Composition of E. huxleyi Strains During a Time Course of Lytic Infection We examined the polar membrane composition of uninfected and EhV86-infected sensitive (Ehux374) and resistant (Ehux373) E. huxleyi strains during a time course of lytic infection (e.g. 52 h post-infection). Using high performance liquid chromatography/electrospray ionization mass spectrometry (HPLC/ESI-MS) (Van Mooy et al., Nature, 458: 69-72, (2009)) we compared the lipid composition of uninfected and infected host cells. We detected glycosylated sphingosine-like lipids in uninfected host cells (GSLs) that appeared to be composed of predominantly hydroxylsphingoid bases derived from palmitoyl-CoA (FIG. 1A). These host sphingoid bases are consistent with the expected products of the host SPT which utilizes palmitoyl-CoA and are common in plants (Lynch and Dunn, *New Phytol.* 161, 677 (2004)). However, the lipids from EhV86-infected Ehux374 possessed unique GSLs yielding fragmentation ions that were clearly indicative of multiply-hydroxylated sphingoid bases derived from myristoyl-CoA (FIG. 1B). Additional structural information is presented in FIGS. 9 and 10. These sphingoid bases are the expected products of viral serine palmitoyltransferase (SPT), based on the aforementioned preference for myristoyl-CoA. The viral-induced myristoyl-base glycosylated sphingosine-like lipids GSLs were absent in uninfected cells and were unique to lytic viral infection (FIG. 1B). Both resistant and susceptible hosts produced significant concentrations of host palmitoyl GSLs, which were structurally different from the viral myristoyl GSLs (FIG. 1A, D).

Figure 1C:
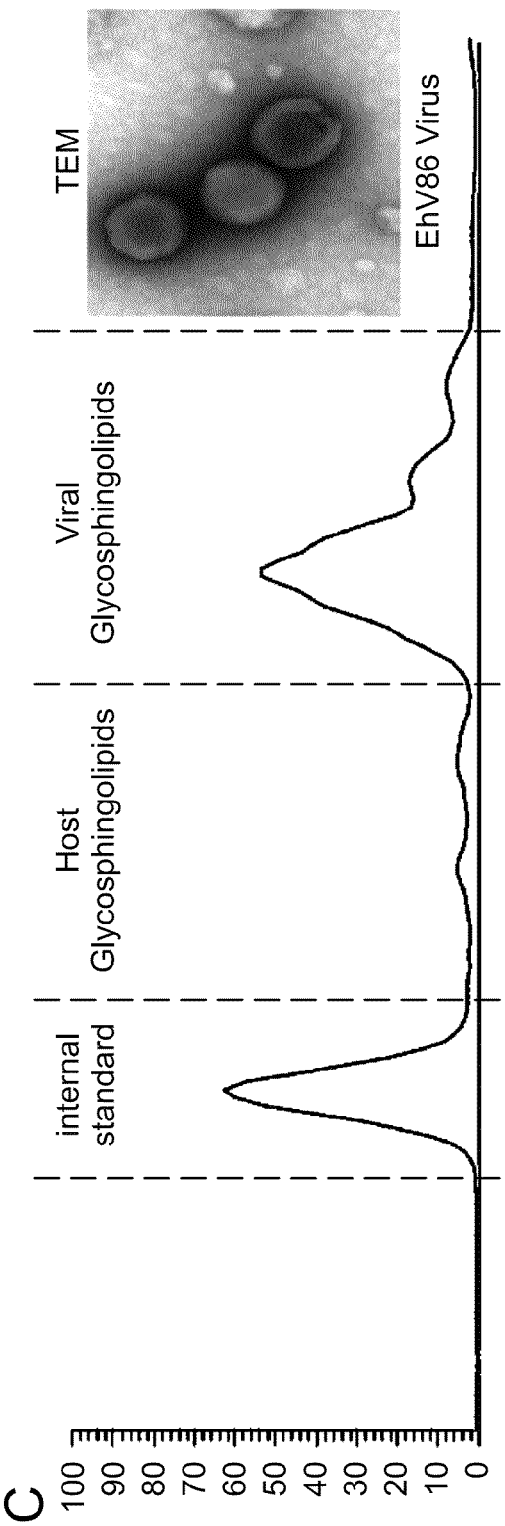

To definitively ascertain the origin of the myristoyl GSLs, viruses were purified using a cesium chloride ($CsCl_2$) density gradient and ultracentrifugation. Identical myristoyl GSLs were dominant components of the lipids extracted from purified EhV86 viruses. Furthermore, host palmitoyl GSLs were absent in the purified viruses. These observations strongly suggest that the viral GSLs are an inherent and important component of the membranes underlining the capsid layer (FIG. 1C). Transmission electron microscopy (TEM) of infected Ehux374 cells revealed a structural pattern of viral particles within intra cytoplasmic vacuoles (FIG. 1C-inset). Similar structures have also been observed in other giant viruses, such as Mimivirus, which produces specialized viral factories and cytoplasmic replication centers (Suzan-Monti et al., PLoS ONE 2, e328 (2007)). Previous proteomic analysis of EhV-86 virion determined that 23 of a total of 28 proteins are predicted to be membrane proteins (Allen et al., Proteome Sci. 6 (2008)), corroborating our observations of GSLs and membrane structures. Sphingosine-like lipids such as GSLs are ubiquitous constituents of membrane lipids (e.g., lipid rafts) in eukaryotes. Accumulating data suggest that lipid rafts may be involved in the entry and budding of HIV and Hepatitis C, yet their role is not well understood (Brügger et al., Proc. Natl. Acad. Sci. USA. 103, 2641 (2006), Sakamoto et al., Nat Chem Biol 1, 333 (2005)). While sphingolipids are distributed in some prokaryotes, they have never been found in non-enveloped viral membranes (Brügger et al., Proc. Natl. Acad. Sci. USA. 103, 2641 (2006)).

The dramatic accumulation of viral GSLs in Ehux374 during EhV86 infection was accompanied by a dramatic reduction in cell abundance, severely compromised photosynthetic efficiency (declining to 0.22 after 48 h), and ~30 fold induction in caspase specific activity. The potent induction of this fundamental biochemical PCD marker occurred concomitantly with de novo synthesis of viral GSLs and viral production, both signaling the demise of Ehux374 at the onset of the lytic phase at 25 h post-infection. Basal production of viral GSLs began within the first 3.5 h (FIG. 2D), corroborating gene expression data for the virally encoded SPT as early as 2 h post-infection (Allen et al., J. Virology 80, 7699 (2006)). At an advanced state of infection, caspase specific activity and GSL production reached more than 100 fold the levels seen in uninfected cells or in resistant Ehux373 cells (FIG. 2C, 2D).

Figure 1D:
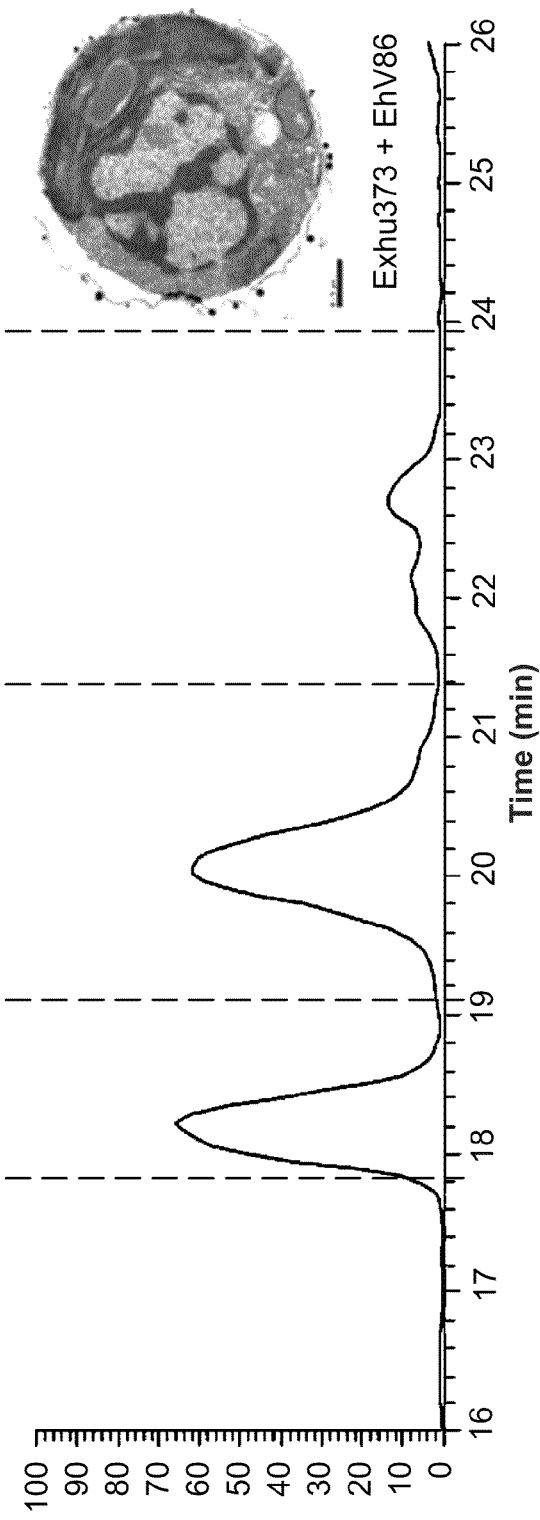
Figure 2A:
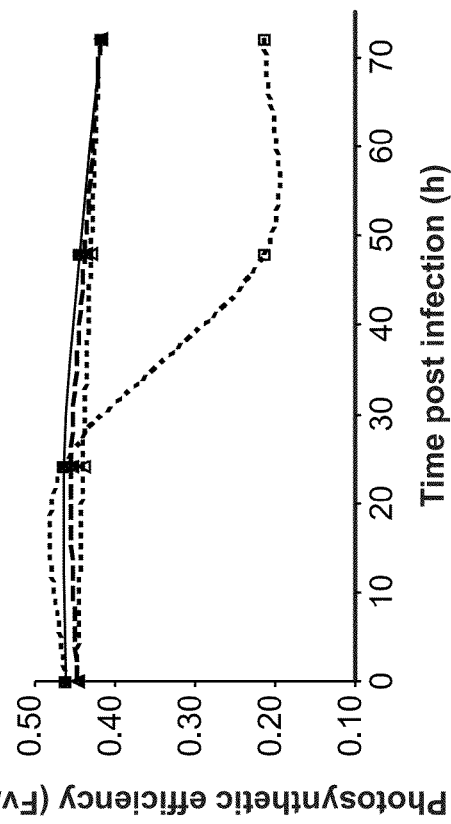
FIG. 2 illustrates the onset of the lytic phase during EhV86 infection is mediated by induction of caspase specific activity and viral GSLs production. Viral infection dynamics of susceptible Ehux374 or resistant Ehux373 strains as monitored by the following parameters: host abundances (FIG. 2A), photochemical quantum yield of photosystem II (Fv/Fm) (FIG. 2B), caspase specific activity (cleavage of IETD-AFC in cell extracts) (FIG. 2C), and de novo synthesis of viral, myristoyl GSLs (FIG. 2D).
Figure 2B:
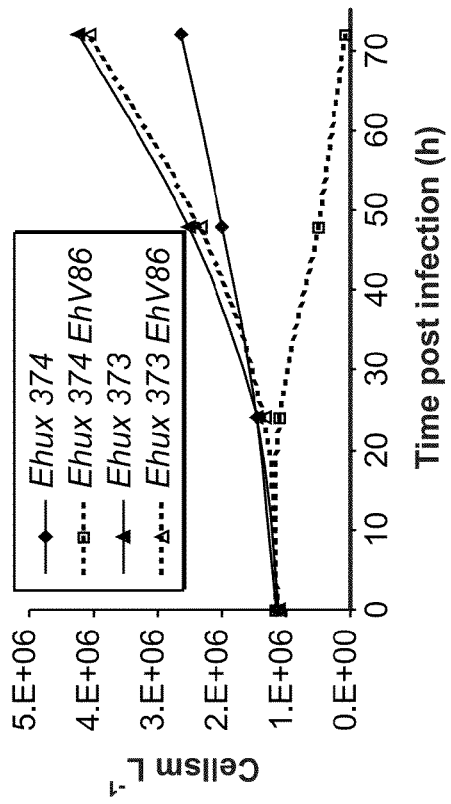
Figure 2C:
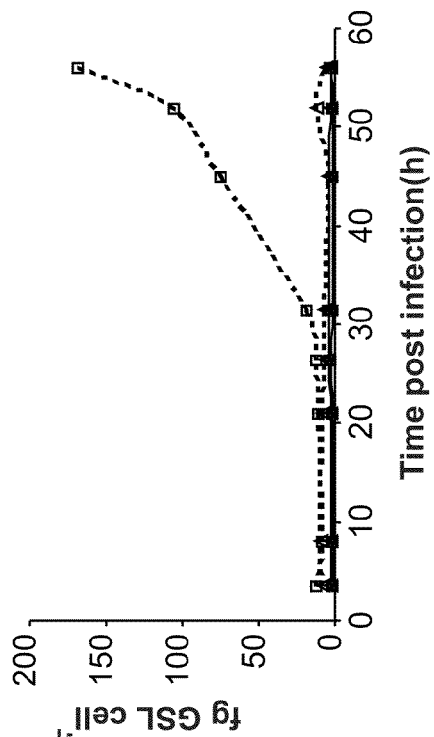
Figure 2D:
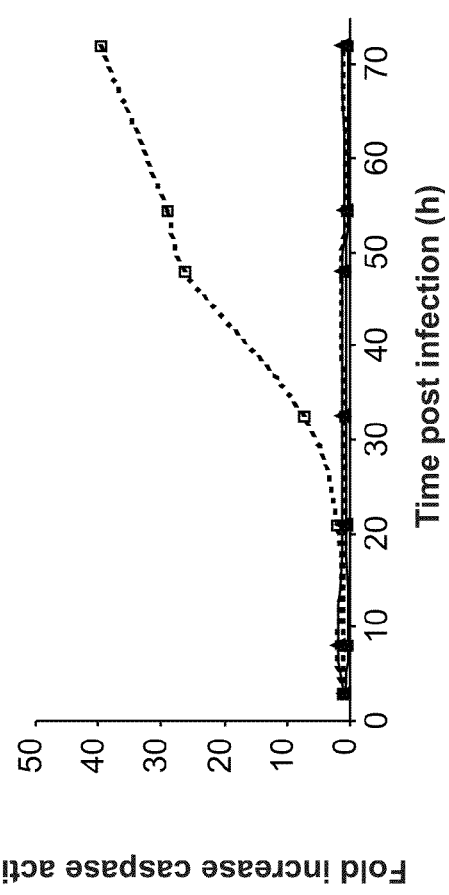

In contrast, Ehux373 strain displayed resistance to EhV86 infection, exhibiting slightly better growth than control, uninfected Ehux374 cells (FIG. 2A). Photosynthetic health, cell abundance, and caspase specific activity in infected Ehux373 perfectly paralleled the dynamics of uninfected Ehux373 cells through the course of the experiment (FIG. 2A-C). Only trace levels of viral GSLs were detected in infected Ehux373, likely a signature of the EhV86 inoculum (FIG. 2D and FIG. 1D). Both resistant and susceptible hosts produced significant concentrations of host palmitoyl GSLs, which were structurally different from the virally associated myristoyl GSLs (FIG. 1A, D).

Example 2

Bioactive Potential of Viral Glycosylated Sphingosine-Like Lipids

Figure 3A:
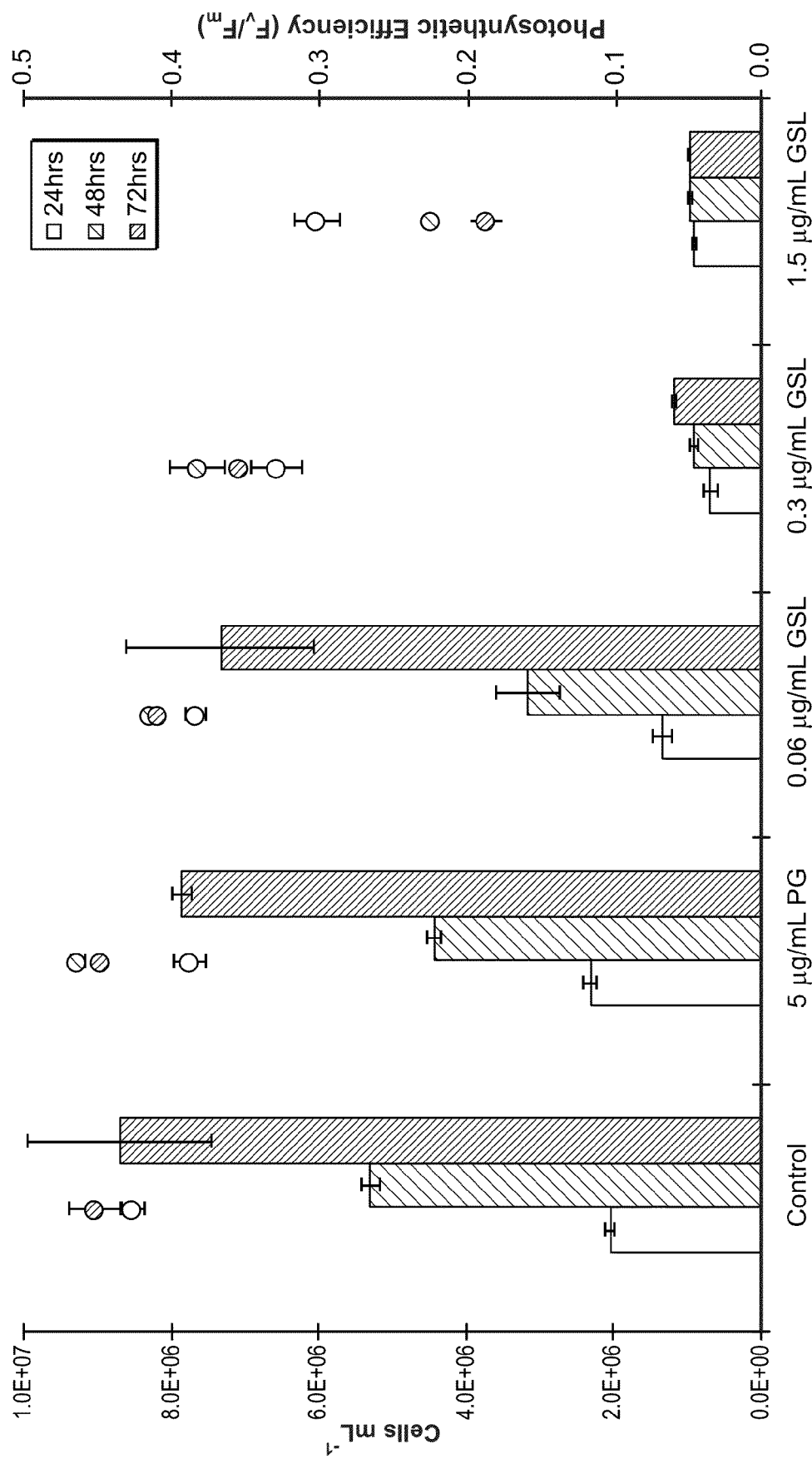
FIG. 3 shows the biomimicry of viral infection mediated by purified viral GSLs. Viral GSLs were applied to uninfected *E. huxleyi* cells and induced PCD. Dose-dependent induction of cell death in uninfected Ehux374 cells over 72 h by application of purified GSLs (0.06, 0.3, 1.5 µg/mL). Cell abundance (cells $ml^{-1}$; bars) and photochemical quantum yield of photosystem II (Fv/Fm; circles) (FIG. 3A), and in vivo caspase activity (measured by flow cytometry) (FIG. 3B). Cytograph plots represent the fluorescence distribution for CaspACE-stained samples in respective treatments after 48 h. The percentage of positively stained cells is given in each panel. Dashed line represents the threshold fluorescence above which cells are positively stained, determined by unstained controls of each treatment. Images of GSL-treated cultures exhibited massive cell lysis after 72 h (FIG. 3C). The percentage of SYTOX positive cells is given for 72 h treatments (inset) and serves as a proxy for dying cells. Control treatments consisted of DMSO (solvent) and the membrane phospholipid phosphatidylglycerol (PG).
Figure 3B:
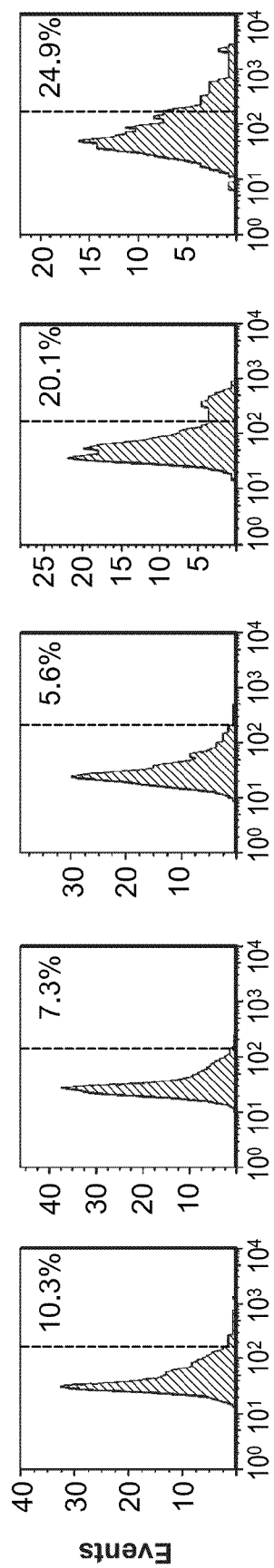
Figure 3C:
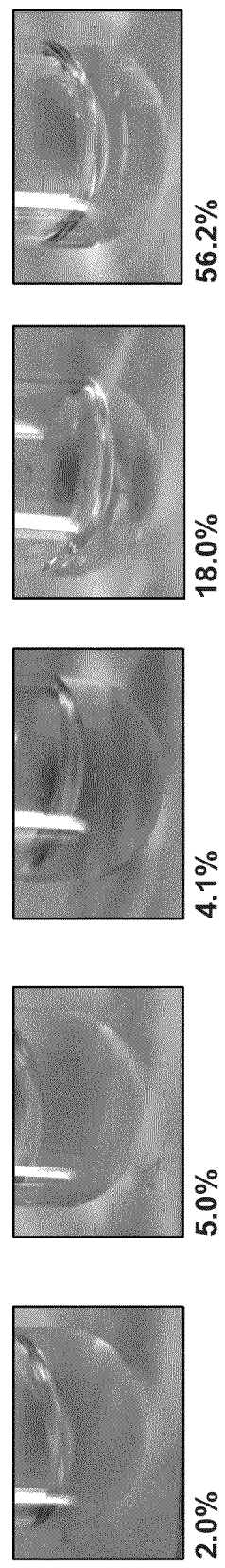

The strong correlation between the initiation of viral lysis, induction of caspase activity, and increase of viral GSLs, motivated us to examine their bioactive potential and ability to modulate host physiology over 72 h at various concentrations (0.06, 0.3, 1.5 µg/mL) (FIG. 3). We purified the viral GSLs from EhV86-infected Ehux374 cells by preparative HPLC. Their application had a remarkable effect on cell fate. They severely suppressed cell growth compared to control cells treated with DMSO (solvent) and control cells treated with phosphatidylglycerol (PG), which had a similar HPLC retention time (FIG. 3A). Cells treated with viral GSLs exhibited a dose-dependent induction of cell death above a distinct threshold concentration. Induction of cell death was accompanied by compromised photosynthetic efficiency (FIG. 3A, Fv/Fm) and the induction of in vivo caspase activity assessed through the cell staining with a fluorescently-labeled, broad spectrum caspase inhibitor, VAD-FMK-FITC (FIG. 3B and inset). Positive staining of Ehux374 cells was only observed for photosynthetic impaired cells, identified by their weak chlorophyll autofluorescence (data not shown). Approximately 20-25% of Ehux374 cells treated with 0.3 and 1.5 µg/ml GSLs had elevated caspase activity after 48 h, reaching up to 35% after 72 h (FIG. 3B). Likewise, up to 18% and 56.2% of the cells were SYTOX positive at 0.3 and 1.5 µg/mL GSLs, respectively (FIG. 3C), indicative of compromised cell membrane integrity late in the cell death cascade and consistent with findings of phytoplankton PCD triggered by abiotic stresses (Vardi et al., Curr. Biol. 9, 1061 (1999)). Less than 5.8-10.2% of cells were positively stained in the control treatments and in cells that were treated with a sub-lethal GSL concentration (e.g. 0.06 µg/mL), indicating low mortality in these cells. A visual comparison of control (DMSO, PG) and GSL treatments>0.06 µg/mL clearly revealed massive cell lysis in the latter (FIG. 3C). Notably, nearly identical cell death dynamics were observed between viral infection and cell death induced by application of purified, viral GSLs (compare FIG. 2A-C and FIG. 3).

Given their potent ability to trigger E. huxleyi's PCD response in a dose-dependent manner and their presence in purified EhV virions, viral GSLs may be part of an elegant timing mechanism for viral release. In such a mechanism, host lysis is dependent on the accumulation of viral myristoyl GSLs to a critical effective concentration, above which host PCD is induced. According to our measurements, an EhV86 virion contains ~0.1-0.3 fg of myristoyl GSLs. At a typical burst size of ~800-1,000 viruses cell$^{-1}$ (Bidle et al., Proc. Natl. Acad. Sci. USA. 104, 6049 (2007)), an effective intracellular concentration of ca. 100 fg cell$^{-1}$ is reached; this concentration is identical to the 100-200 fg cell$^{-1}$ we observed in host cells prior to lysis and is well within the critical threshold concentration for PCD activation (FIG. 2D). This strategy is also consistent with observations of low grade, persistent viral production during early phase infection prior to massive host cell lysis, when the accumulated, internal GSL concentration is too low to induce host PCD.

While not wishing to be bound by any theory, based on our measurements of the cellular production quotas of GSLs (100-200 fg cell$^{-1}$), we believe that such bioactive molecules have the potential to elicit cell death in surrounding, uninfected cells under natural bloom densities, and, hence, act as a bloom termination signal. It has been suggested that one potential evolutionary driver of PCD in unicellular organisms is a 'viral exclusion' strategy (Bidle et al., Proc. Natl. Acad. Sci. USA. 104, 6049 (2007)). At E. huxleyi bloom cell abundances (ca. 10,000 cells ml$^{-1}$), lysis may lead to sufficiently high local GSL concentrations sufficient to effectively compromise cell physiology and prevent viral infection through premature death of surrounding cells (see FIG. 3). Similar findings were recently reported for diatom-derived oxylipins found to act as infochemicals to either potentiate PCD or to induce resistance in sub-lethal doses (Vardi et al., Curr. Biol. 18, 895 (2008), Vardi et al., Plos Biology 4, 411 (2006)).

Taken together, these observations demonstrated that viral GSLs have a critical role in inducing caspase activity and host PCD in a dose-dependent manner. These viral "toxins" can biomimic viral infection and induce PCD in uninfected E. huxleyi cells, a process that is essential for successful virus infection (Bidle et al., Proc. Natl. Acad. Sci. USA. 104, 6049 (2007)). In contrast, inhibition of caspase activity in infected Ehux374 cells severely impaired viral propagation, improved photosynthetic efficiency, and significantly prolonged host survival (Bidle et al., Proc. Natl. Acad. Sci. USA. 104, 6049 (2007)). Viral toxin analogs have also been found in cytoplasmic persisting double-stranded RNA viruses where three different 'killer toxins' induced caspase-mediated apoptosis in yeast (Reiter et al., J. Cell Biol. 168, 353 (2005)). GSLs have been specifically found to act as effective elicitors in a wide range of phytopathogens by inducing the accumulation of antimicrobial compounds (phytoalexins), cell death, and increased resistance to subsequent infection by compatible pathogens in rice plants (Koga et al., J. Biol. Chem. 273, 31985 (1998)). Elevated ceramide concentrations have also been implicated in modulation of endocytic pathways and lipid raft microdomain formation (Grassme et al., Nat Med 9, 322 (2003)). Consequently, ceramide enrichment of plasma membranes can serve to modulate entry, replication and release of viruses (Brügger et al., Proc. Natl. Acad. Sci. USA. 103, 2641 (2006), H. Sakamoto et al., Nat Chem Biol 1, 333 (2005)). GSL enrichment in an intact EhV86 virions and profound accumulation during lytic phase may suggest similar function.

Example 3

Host Resistance to Lytic Viral Infection

In contrast to PCD induced by viral glycosylated sphingolipids in sensitive strains of E. huxleyi, host resistance was characterized by the absence of toxic viral GSLs and caspase activity, both of which are required to induce PCD (FIG. 2). We detected unique lipids in resistant strains that were absent from susceptible strains, shedding insight into a potential molecular basis for viral resistance, aside from the induced sexual differentiation mechanism to evade viral infection.

Figure 4:
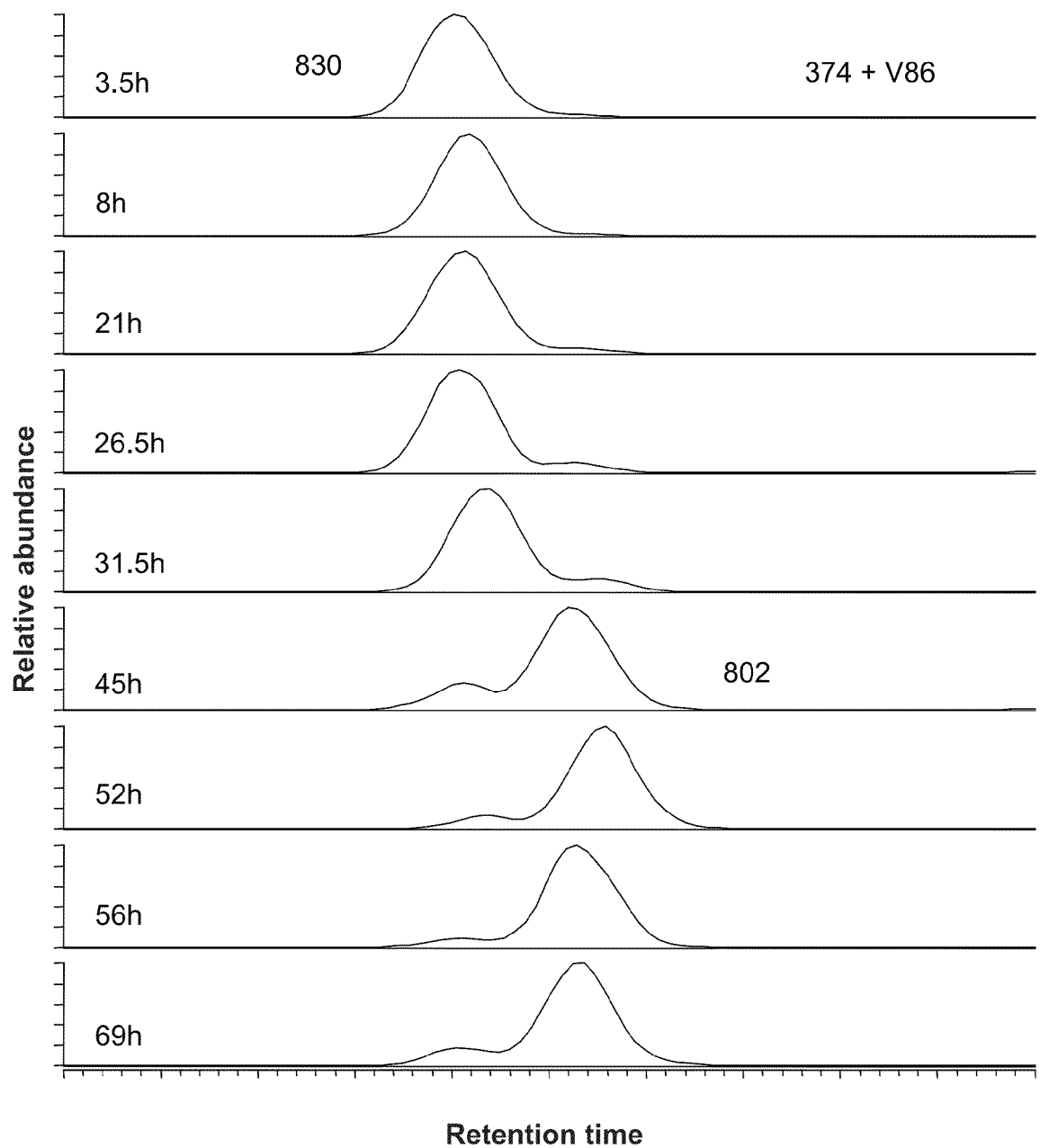
FIG. 4 is a detailed profile of lipids conferring resistance to viral infection. A dramatic induction of the lipids (called 802 lipids) (>100 fold above baseline) is clearly observed only in sensitive strain Ehux374 during the onset of lytic phase. Concomitant with the induction of 802, a major reduction in the lipids (called 830 lipids) occurred during the lytic phase.
Figure 5:
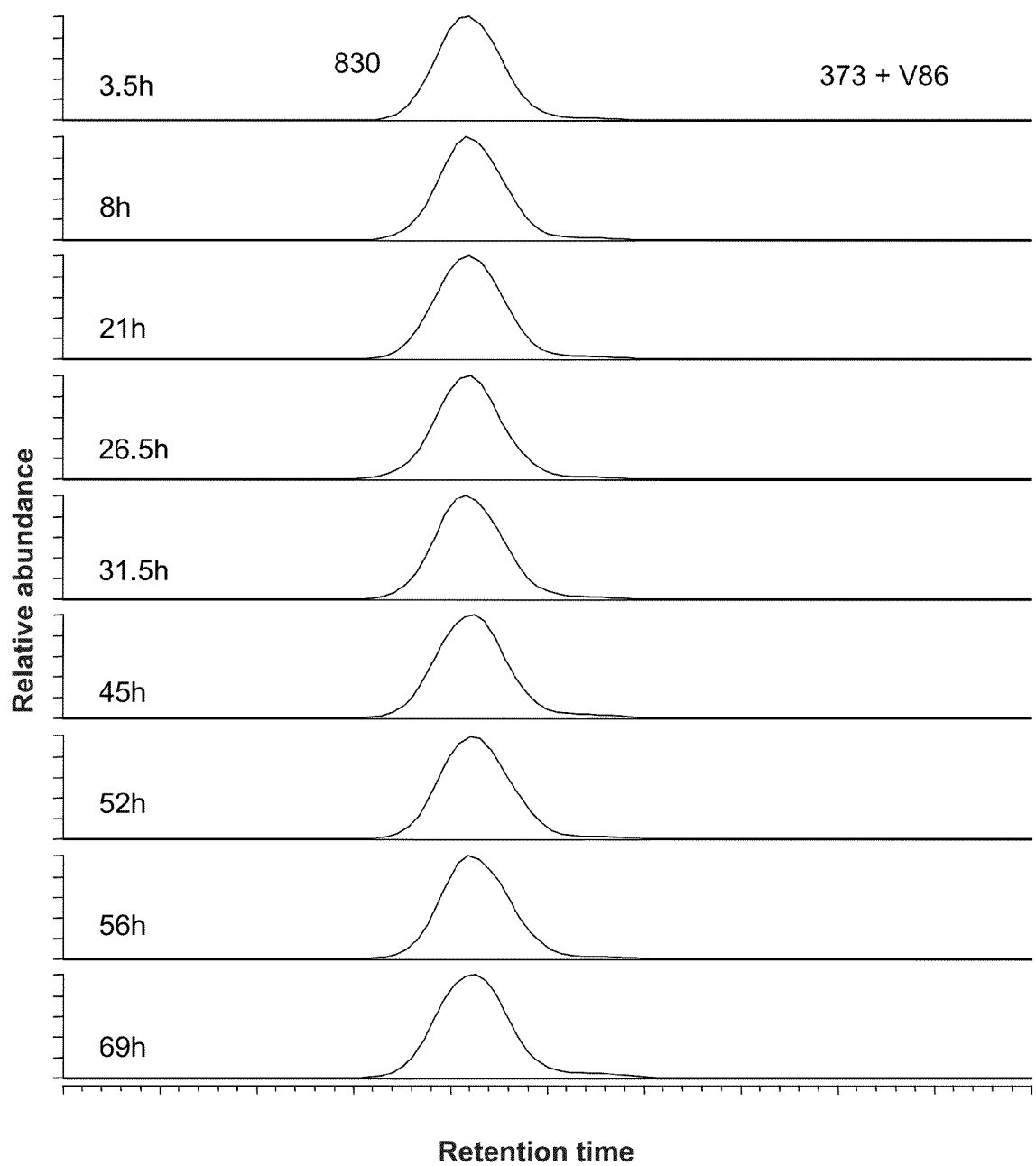
FIG. 5 shows the absence of induction of the 802 lipids in resistant strain Ehux373. The 802 lipids are not induced in resistant strain Ehux373 and levels of the 830 lipids remain constant.
Figure 6A:
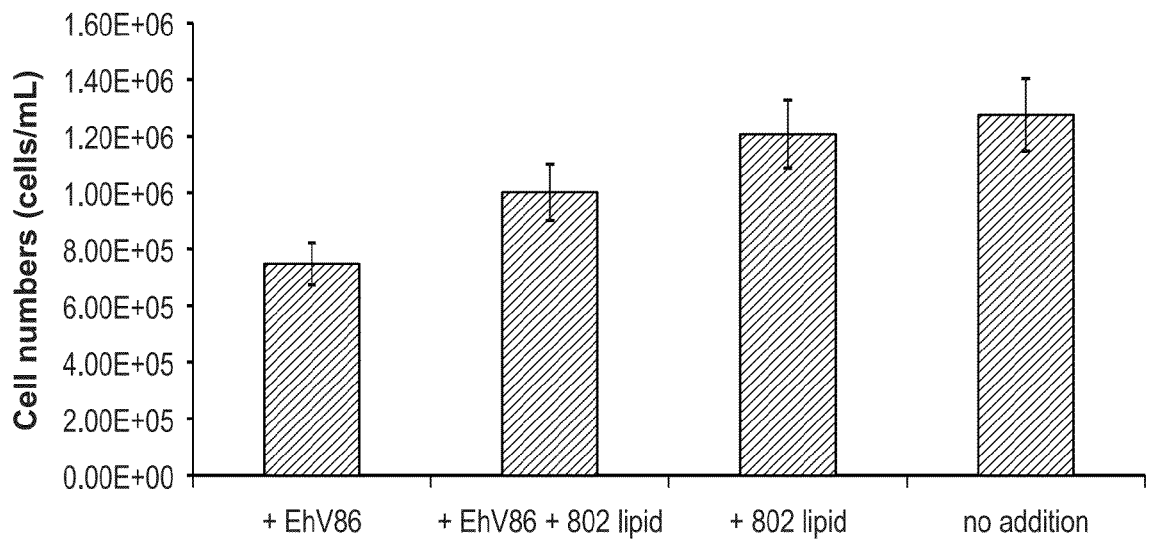
FIG. 6A shows cell growth of Ehux374 in the presence or absence of EhV86, with or without the 802 lipid.
Figure 6B:
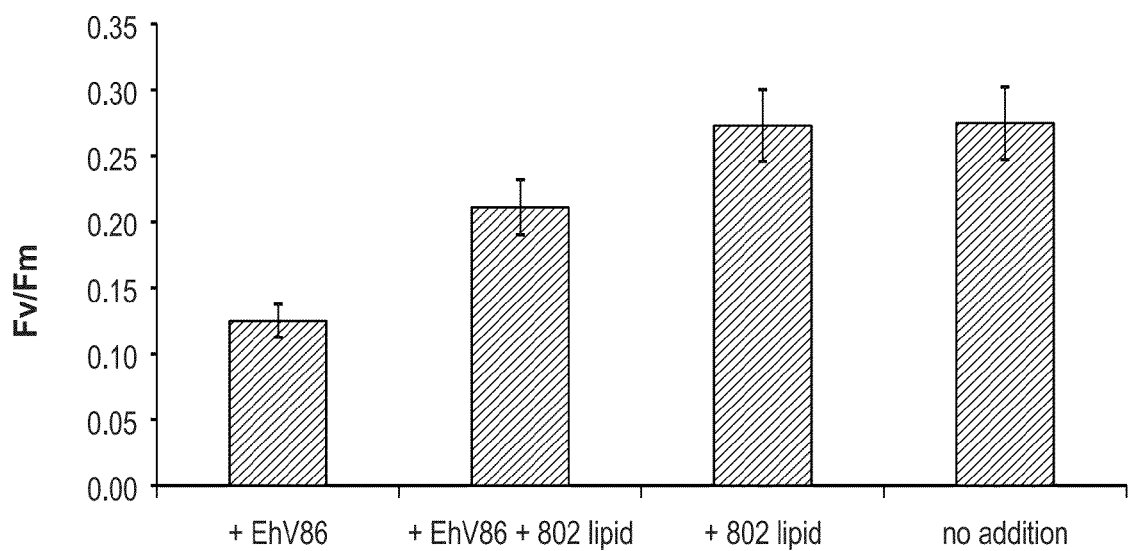
FIG. 6B shows the photosynthetic efficiency, as measured by photochemical quantum yield of photosystem II (Fv/Fm).
Figure 7:
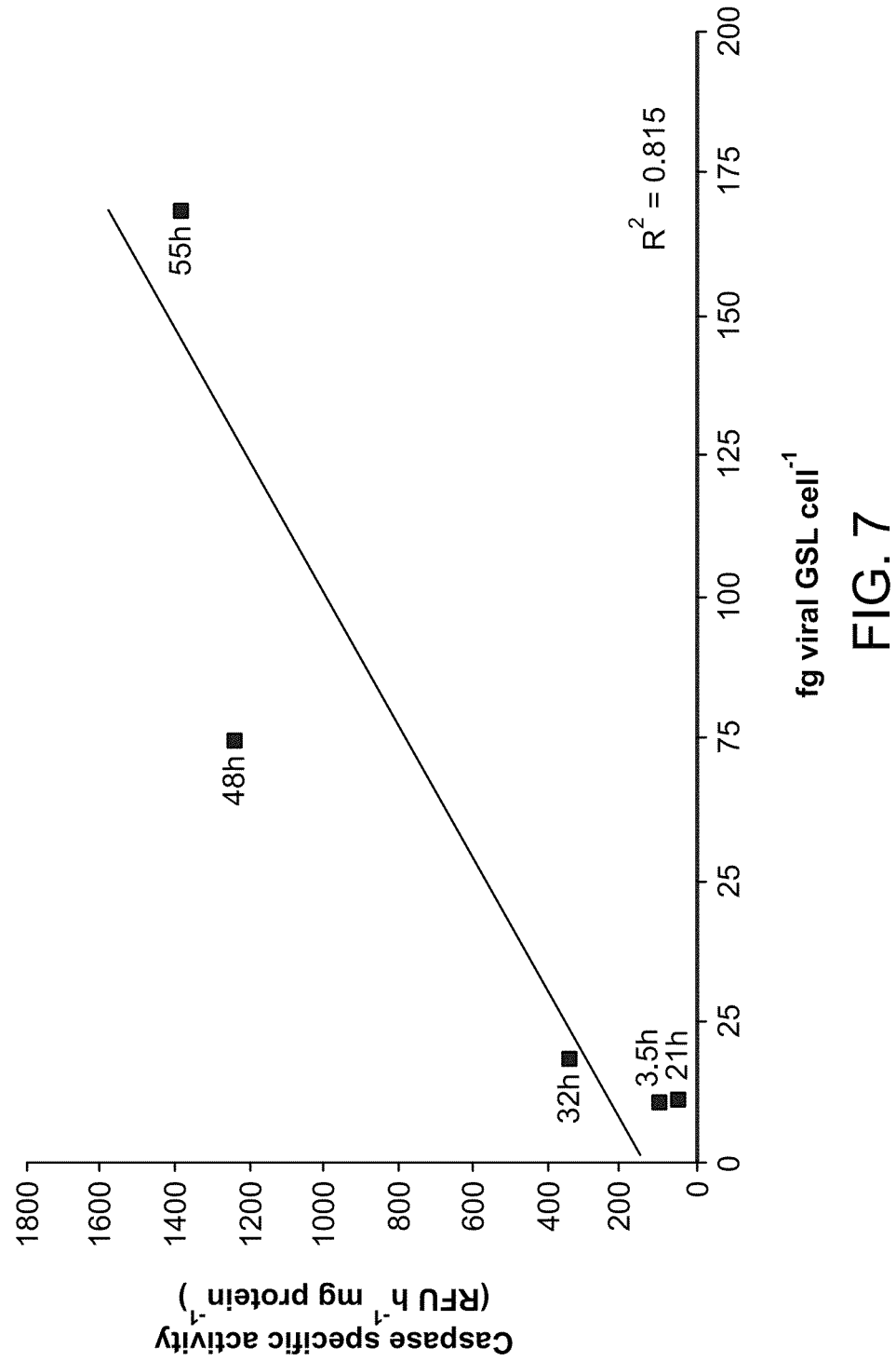
FIG. 7 shows the linear regression between cellular, viral GSL production and caspase specific activity (hydrolysis rates of IETD-AFC) exhibited hight correlation during the course of viral infection. Data points represent cells analyzed at different time points during infection.

We explored the abundance of the groups of other lipids (herein called 830 lipids and 802 lipids). Detailed profiles of these lipids are depicted in FIGS. 4 and 5 during the course of viral infection. A dramatic induction (>100 fold) of 802 is clearly observed only in sensitive strain Ehux374 during the onset of lytic phase (FIG. 4) and not by infected Ehux373 resistant strain (FIG. 5). Concomitant with the induction of 802, a major reduction in 830 occurred during the lytic phase. Preliminary data on the biological activity of 802 has revealed prolonged survival of more than 25% Ehux374 population during viral infection both in term of photosynthetic health (FIG. 6B) and cell growth (FIG. 6A). Hence, this compound may effectively protect host cells against successful viral infection, allowing a significant subpopulation to survive.

Material and Methods

Assessment of Cell Growth and Physiology

Emiliana huxleyi strains CCMP 373 and 374 were obtained from the Provasoli-Guillard Center for Culture of Marine Phytoplankton (CCMP) and batch grown in f/2 medium (minus Si) at 18° C., 14:10 (L:D) cycle and ≈150 µmol quanta m$^{-2}$·s$^{-1}$ with constant aeration. Cell abundance was determined by using a Coulter Multisizer II (Beckman Coulter, Fullerton, Calif.). Fluorescence Induction and Relaxation System (FIRe; Satlantic Instruments) was used to derive the maximum photochemical quantum yield of photosystem II (Fv/Fm), an indicator of photosynthetic health (Kolber et al., Biochim. Biophys. Acta 1367, 88 (1998)).

EhV86 Isolation

Viral particles were purified from a lysate of *E. huxleyi* CCMP strain 374 culture infected with EhV-86. Briefly, host cells were cultured in 10 liters of f/2 medium at 18° C. in 14 h: 10 h light-dark illumination. Exponentially growing ($1.5 \times 10^6$ cells $ml^{-1}$) cells were infected with fresh EhV-86 lysate. Once clearing of the host culture was observed (5 days later), the lysate was passed through a GF/F and 0.45 µm pore size Strivex filters; The filtrate was concentrated by tangential flow filtration (Vivaflow200, 50 kDa Sartorius) to 50 ml, according to manufacture instructions. Virus particles were purified by $CsCl_2$ gradient (1.1 g/ml, 1.2 g/ml, 1.3 g/ml, 1.4 g/ml) ultracentrifugation at 25000 rpm at 22° C. for 2 h in a SW41 Ti Beckman rotor. The virus band was removed with a syringe and filtered on a precombusted 0.02 µm Anodisc filter, and immediately frozen in liquid $N_2$ for lipid analysis. The presence of EhV86 virions in the purified viral fraction was verified by PCR amplification with specific capsid primers (Schroeder et al., Arch. Virol. 147, 1685 (2002)) and epifluorescence microscopy following SYBR Gold (Invitrogen) staining (Bidle et al., Proc. Natl. Acad. Sci. USA. 104, 6049 (2007)).

Measurement of Caspase Activity and Cell Death

Cells were pelleted via centrifugation, frozen immediately in liquid nitrogen, and stored at −80° C. until processing for subsequent biochemical analyses. Pellets were resuspended in caspase activity buffer (50 mM HEPES pH 7.3, 100 mM NaCl/10% sucrose/0.1% CHAPS/10 mM DTT) and sonicated. Cellular debris was pelleted by centrifugation (16,000 g; room temperature; 2 min) as described in (Bidle et al., Proc. Natl. Acad. Sci. USA. 104, 6049 (2007)). Cell extracts were incubated with 50 µM IETD-AFC (Calbiochem, San Diego, Calif.) for 4 h at 20° C. The hydrolysis of IETD-AFC was monitored by measuring the accumulation of the fluorescence in a Spectra Max Gemini XS plate reader (excitation 400 nm, emission 505 nm). In vivo caspase activity was assessed in *E. huxleyi* cells by direct staining with CaspACE FITC-VAD-FMK (Promega, Madison Wis.). Cells were pelleted by centrifugation, washed once with PBS (pH 7.5), and resuspended in PBS before the addition of CaspACE (final concentration, 20 µM). Cells were stained for 20 min at 18° C. in the dark, after which they were pelleted by centrifugation, washed once with PBS, fixed with 2% formalin/PBS, and stored at 4° C. until analyzed. Cells were visualized by epifluorescence microscopy using an Olympus IX71 inverted microscope and analyzed for percentage of positive cells at 520 nm using an InFlux Model 209S Mariner flow cytometer and high-speed cell sorter (BD Biosciences). DMSO-treated cells served as controls and were used to gate negatively stained *E. huxleyi* cells, since viral myristoyl GSLs were reconstituted in DMSO. Cell death was also determined by assaying the plasma membrane integrity with SYTOX Green (Invitrogen), a fluorescent DNA-binding dye that is excluded from viable cells. After 15 minutes of incubation with 1 µM SYTOX in the dark, cells were washed with filtered seawater, quantified by screening 400-600 cells via epifluorescence microscopy (FITC filter; 480 nm excitation and 525 nm emission).

Transmission Electron Microscopy (TEM)

Cells were pelleted, washed with 0.2-µm filtered seawater, and preserved in Trump's EM fixative (4% formaldehyde/1% glutaraldehyde in phosphate buffer, pH 7.2) for at least 4 h at 4° C. Fixed cells were rinsed three times in Milloning's phosphate buffer, pH7.3, postfixed for 2 h in 1% buffered $OsO_4$, washed three times, and dehydrated through a graded series of ethanol. After replacement of ethanol with propylene oxide, cells were embedded in Epon-Araldite mixture. Sections were cut by using a LKB 2088 ultramicrotome, collected on 200-mesh copper grids, and stained with uranyl acetate and lead citrate. The stained sections were photographed in a JEM-100CXII electron microscope.

Lipid Analysis

*E. huxleyi* cells were collected by filtration on precombusted GF/F filters, which were snap frozen in liquid nitrogen. Subsequently, lipids were extracted using a modified Bligh-Dyer method, as described (Van Mooy et al., Proc. Natl. Acad. Sci. USA 103, 8607 (2006)). Cellular polar membrane lipids were analyzed by HPLC/ESI-MS as described (Sturt et al. Rapid Comm. Mass Spectrom. 18, 617 (2004)) using an Agilent 1100 HPLC and Thermo Finnigan LCQ Deca XP ion-trap mass spectrometer. Authentic glycosphingolipid standards (Avanti Polar Lipids, brain cerebrosides) were used for initial identification of retention times and to identify characteristic $MS^2$ and $MS^3$ fragmentation; these authentic standards were also used to construct standard curves for quantification. A subset of the samples were analyzed using identical HPLC and ESI conditions on a Thermo FTQ high-resolution Fourier-transform ion cyclotron resonance mass spectrometer (FT-MS) for confirmation of elemental formulas in glycosphingolipid molecular ions and $MS^2$ fragment ions.

Trimethylsilyl Derivatization of Intact Poly-Hydroxylated Glycosyl Cerebrosides (CRBs)

Poly-hydroxylated CRBs were isolated by preparative HPLC from a culture of *E. huxleyi*. An aliquot was dissolved in pyridine and reacted with BSTFA+1% TMCS at room temperature for 4 hours. The mixture was infused directly using a syringe pump into the electrospray source of a LCQ Deca XP ion-trap mass spectrometer. (BSTFA=N,O-Bis(trimethylsilyl)trifluoroacetamide, TMCS=trimethylchlorosilane).

Acid Hydrolysis of Poly-Hydroxylated Glycosyl Cerebrosides (CRBs)

An aliquot of purified poly-hydroxylated CRBs were dissolved in 0.5 N methanolic HCl and reacted overnight at 70° C. Fatty acid methyl esters (FAMEs) were extracted into hexane, sugar moieties were extracted into water, both fractions were dried down, dissolved in pyridine and trimethylsilylated with BSTFA+1% TMCS at 70° C. for 3 hours. Analysis was by GCMS.

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

REFERENCES

Allen, J. Virology, 80(15) 7699-7705 (2006)
Allen et al., Environmental Microbiology, 9(4) 971-982 (2007)
Allen et al., *Proteome Sci.* 6 (2008)
Bidle and Falkowski. Nature Rev. Microbiol. 2:643-655 (2004)
Bidle et al., PNAS 104(14): 6049-6054 (2007)
Bidle and Bender, Eukaryotic Cell 7:223-236 (2008)
Brügger et al., Proc. Natl. Acad. Sci. USA. 103, 2641 (2006)
Brussard, J. Eukaryotic Microbiology, 51:2, 125-138, (2004)
Brussard, Aquat. Microb. Ecol., 10:105-113, (1996)
Douglas et al., Journal of Immunological Methods 188, 219-228 (1995)
Elstein and Zucker, Experimental Cell Research 211, 322-331 (1994)
Fuhrman, Nature 399:541-548 (1999)
Grassme et al., Nat Med 9, 322 (2003)
Leist et al., The Journal of Immunology 153, 1778-1788 (1994)
Lynch and Dunn, *New Phytol.* 161, 677 (2004)
Khuruna et al., Current Science, 88 (5) 740-752 (2005)
Koga et al., J. Biol. Chem. 273, 31985 (1998)
Kolber et al., Biochim. Biophys. Acta 1367, 88 (1998)
Koopman et al., Blood 84, 5, 1415-1420 (1994)
Parker et al., Ann. Rev. Genet. 42:619-45 (2008)
Reiter et al., J. Cell Biol. 168, 353 (2005)
Sakamoto et al., Nat Chem Biol 1, 333 (2005)
Schroeder et al., Arch. Virol. 147, 1685 (2002)
Sturt et al. Rapid Comm. Mass Spectrom. 18, 617 (2004)
Suttle, Nature Reviews Microbiology, Vol. 5, 801-812 (2007)
Suzan-Monti et al., *PLoS ONE* 2, e328 (2007)
Van Mooy et al., Proc. Natl. Acad. Sci. USA 103, 8607 (2006)
Van Mooy et al., Nature, 458: 69-72, (2009)
Vardi et al., Curr. Biol. 9, 1061 (1999)
Vardi et al., Plos Biology 4, 411 (2006)
Vardi et al., Curr. Biol. 18, 895 (2008)
Vardi et al., Science, 326(5954): 861-5 (2009)
Verhaegen et al., European Microscopy and Analysis (1998)
Wilson et al., Science 209, 1090 (2005)

We claim:

1. A pharmaceutical composition comprising a compound having a structure of formula (I)

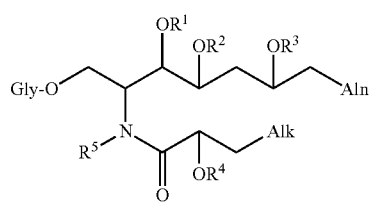

or a pharmaceutically acceptable salt thereof, wherein
Gly is a glycosidic residue;
$R^1$, $R^2$, $R^3$, $R^4$ and $R^5$ are each independently selected from hydrogen, $C_{1-6}$alkyl, and $C_{1-6}$alkylcarbonyl;
Aln is a $C_{2-25}$alkenyl group; and
Alk is a $C_{1-25}$alkyl group, and a pharmaceutically acceptable carrier or diluent.

2. A method for inducing apoptosis in a cancer cell, a lymphocyte that recognizes self-peptides, or a virally-infected cell, comprising contacting the cell or lymphocyte with a pharmaceutical composition according to claim 1.

3. A method for treating cancer in a patient, comprising administering to the patient a pharmaceutical composition according to claim 1.

Figure 9A:
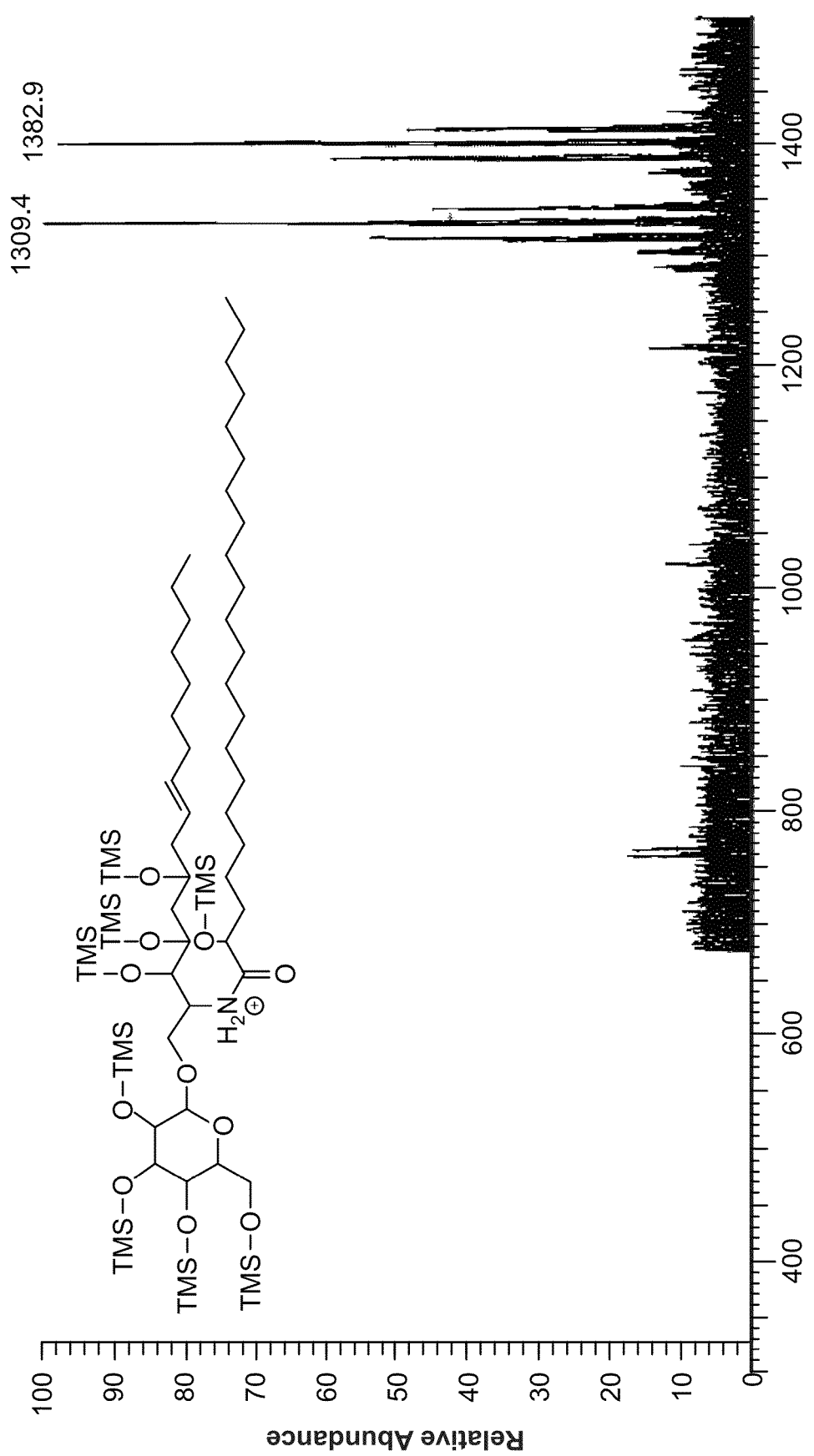
FIG. 9A shows a full scan (m/z 650-1500) in positive ion mode.
Figure 9B:
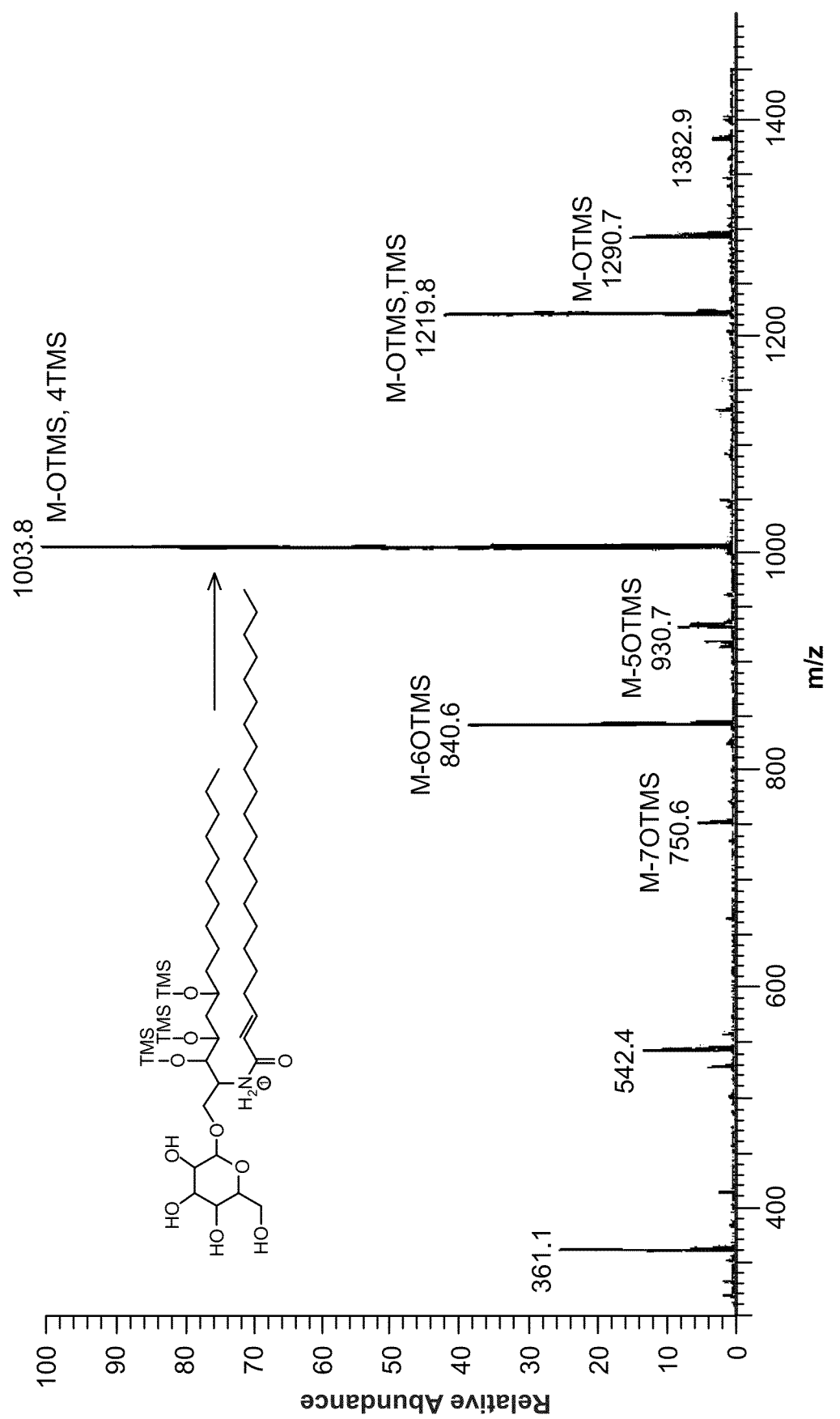
FIG. 9B shows ms/ms fragmentation of 1383. Fully trimethylsilyl (TMS)-derivatized cerebroside, TMS=Si(CH3)3. For the chemical formula $C_{68}H_{150}NO_{11}Si_8$, exact mass is 1380.9. This molecule is observed at a higher m/z of 1382.9 due to isotopic contribution of the molecule, probably due to a sterically hindered hydroxyl group. Smaller peaks on either side of 1309 and 1382 are most likely larger and smaller fatty acid moieties.
Figure 10A:
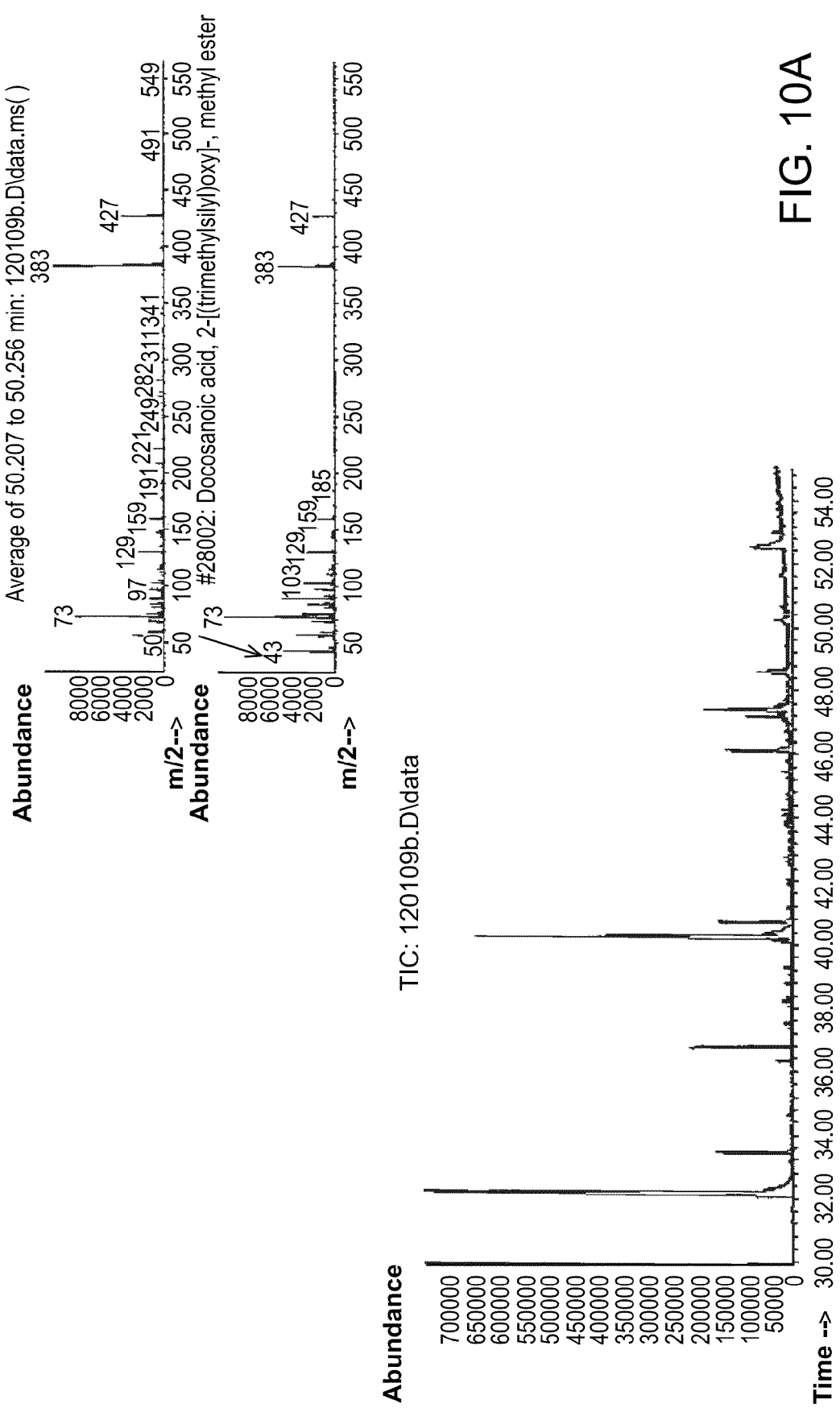
FIG. 10A shows a total ion current chromatogram indicating fatty acid methyl esters of fatty acids released by methanol/acid hydrolysis of poly-hydroxylated cerebrosides isolated from infected EHux and subsequently trimethylsilylated to derivatize any exposed hydroxyl groups. The inset shows a mass spectrum of 2-[oxy(trimethylsilyl)]-docosanoic acid fatty acid methyl ester (top) and a corroborative library match (bottom, 93% confidence level). Larger peaks at 40.2, 36.8 and 33.4 minutes are fatty acid methyl esters of octadecenoic, hexadecanoic and tetradecanoic acids, respectively.
Figure 10B:
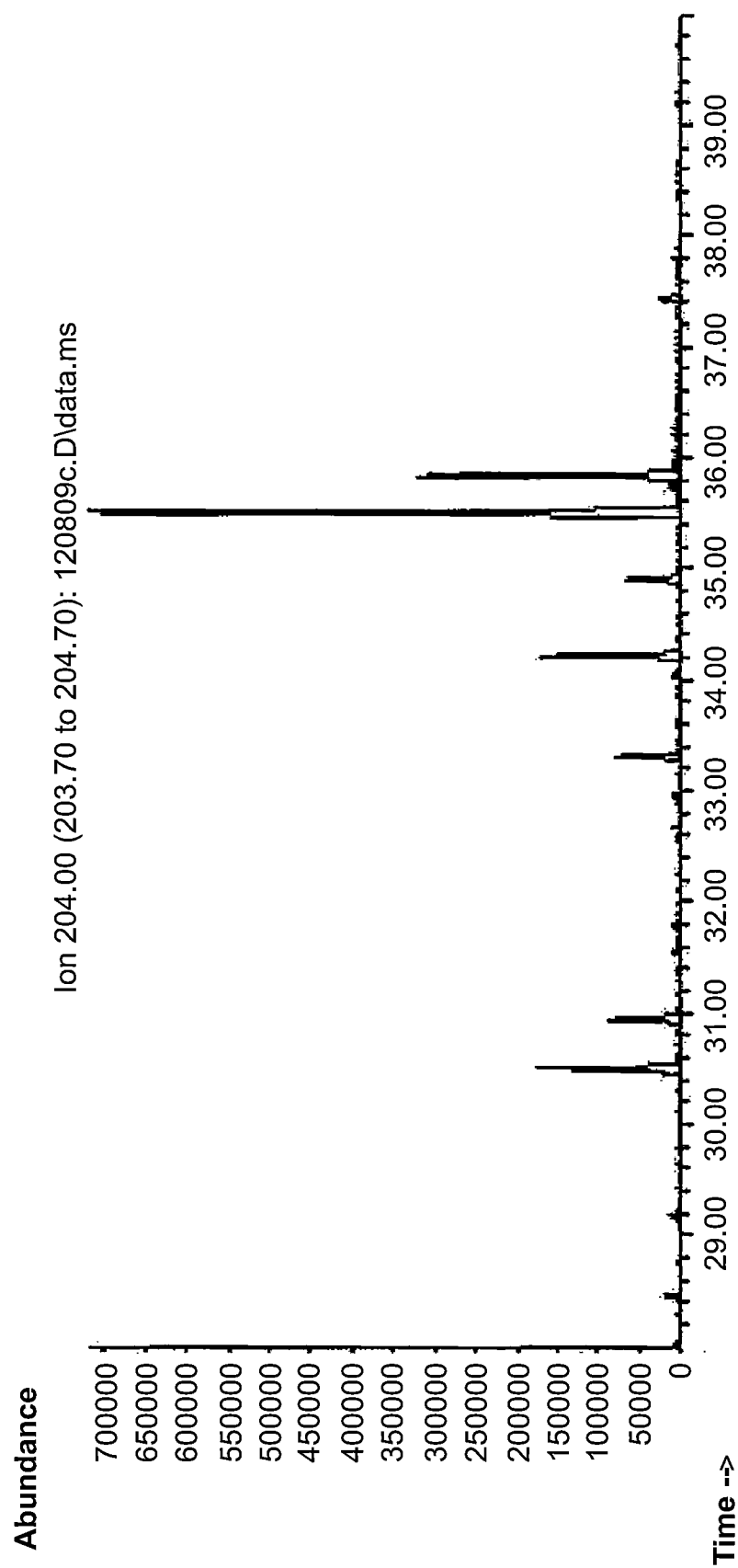
FIG. 10B shows the extracted ion chromatogram (m/z 204) of (trimethylsilyl derivatized) sugar moieties released by acid hydrolysis of poly-hydroxylated cerebrosides isolated from infected EHux. m/z 204 is diagnostic for sugars and peaks are identified (by library match with >80% confidence) as derivatives of mostly α-D-galactose, mannose, glucose and xylose.

4. A pharmaceutical composition comprising a glycerolipid having a mass spectra pattern as shown in FIG. 9A or 9B and a pharmaceutically acceptable carrier or diluent.

5. A method for inducing apoptosis in a cancer cell, a lymphocyte that recognizes self-peptides, or a virally-infected cell, comprising contacting the cell or lymphocyte with a pharmaceutical composition according to claim 4.

6. A method for treating cancer in a patient, comprising administering to the patient a pharmaceutical composition according to claim 4.

7. A pharmaceutical composition comprising a substantially purified bioactive lipid expressed to a greater degree in virally infected than in non-virally infected phytoplankton, of which said bioactive lipid induces apoptosis of phytoplankton in an assay, said assay comprising the steps of:
   (a) contacting the phytoplankton with the bioactive lipid; and
   (b) assaying the phytoplankton for apoptosis-associated activity in the presence of the bioactive lipid;
   wherein apoptosis-induced activity in the phytoplankton indicates that the bioactive lipid induces apoptosis of phytoplankton;
and wherein said bioactive lipid has a structure of Formula (I):

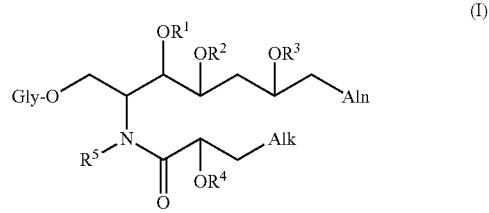

or a pharmaceutically acceptable salt thereof, wherein
Gly is a glycosidic residue;
$R^1$, $R^2$, $R^3$, $R^4$ and $R^5$ are each independently selected from hydrogen, $C_{1-6}$alkyl, and $C_{1-6}$alkylcarbonyl;
Aln is a $C_{2-25}$alkenyl group; and
Alk is a $C_{1-25}$alkyl group and said composition further comprises a pharmaceutically acceptable carrier or diluent.

8. The bioactive lipid containing composition according to claim 7, wherein the bioactive lipid is capable of inducing apoptosis in a cancer cell, a lymphocyte that recognizes self-peptides, or a virally-infected cell.

9. A method for inducing apoptosis in a cancer cell, a lymphocyte that recognizes self-peptides, or a virally-infected cell, comprising contacting the cell or lymphocyte with a pharmaceutical composition according to claim 7.

10. A method for treating cancer in a patient, comprising administering to the patient a pharmaceutical composition according to claim 7.

* * * * *